US009109200B2

(12) United States Patent
Piatesi et al.

(10) Patent No.: US 9,109,200 B2
(45) Date of Patent: Aug. 18, 2015

(54) USE OF ENZYMES TO REDUCE ALDEHYDES FROM ALDEHYDE-CONTAINING PRODUCTS

(75) Inventors: Andrea Piatesi, Mannheim (DE); Tilo Habicher, Speyer (DE); Michael Büschel, Worms (DE); Li-Wen Wang, Mannheim (DE); Jürgen Reichert, Limburgerhof (DE); Rainer Packe-Wirth, Trostberg (DE); Kai-Uwe Baldenius, Heidelberg (DE); Erich Kromm, Weisenheim am Sand (DE); Stefan Häfner, Speyer (DE); Carsten Schwalb, Mannheim (DE); Hans Wolfgang Höffken, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 357 days.

(21) Appl. No.: 13/262,662

(22) PCT Filed: Mar. 31, 2010

(86) PCT No.: PCT/EP2010/054284
§ 371 (c)(1),
(2), (4) Date: Oct. 3, 2011

(87) PCT Pub. No.: WO2010/115797
PCT Pub. Date: Oct. 14, 2010

(65) Prior Publication Data

US 2012/0028333 A1 Feb. 2, 2012

(30) Foreign Application Priority Data

Apr. 7, 2009 (EP) .................................... 09157522

(51) Int. Cl.

| | |
|---|---|
| ***C12N 9/06*** | (2006.01) |
| ***C11D 3/386*** | (2006.01) |
| ***C12N 15/00*** | (2006.01) |
| ***C12N 1/20*** | (2006.01) |
| ***C12P 7/00*** | (2006.01) |
| ***C07H 21/04*** | (2006.01) |
| ***C12N 9/02*** | (2006.01) |
| ***C12N 15/63*** | (2006.01) |
| ***D06M 16/00*** | (2006.01) |
| ***D06M 15/423*** | (2006.01) |
| ***D06P 1/00*** | (2006.01) |
| ***D06P 1/56*** | (2006.01) |

(52) U.S. Cl.
CPC .......... *C12N 9/0008* (2013.01); *C11D 3/38654* (2013.01); *C12N 15/63* (2013.01); *C12P 7/00* (2013.01); *D06M 15/423* (2013.01); *D06M 16/003* (2013.01); *D06P 1/0004* (2013.01); *D06P 1/56* (2013.01)

(58) Field of Classification Search
CPC .. C12N 9/0008; C12N 15/63; C11D 3/38654; C12P 7/00
See application file for complete search history.

(56) References Cited

U.S. PATENT DOCUMENTS

| | | | |
|---|---|---|---|
| 4,559,097 | A | 12/1985 | Janiga |
| 5,071,945 | A | 12/1991 | Weichmann et al. |
| 5,352,274 | A | 10/1994 | Blakley |
| 5,795,933 | A | 8/1998 | Sharp et al. |
| 5,830,414 | A | 11/1998 | Ishii et al. |
| 6,265,589 | B1 | 7/2001 | Hois et al. |
| 6,596,520 | B1 | 7/2003 | Friedrich et al. |
| 2010/0184121 | A1 | 7/2010 | Misiak et al. |

FOREIGN PATENT DOCUMENTS

| | | | |
|---|---|---|---|
| EP | 0 336 165 | A2 | 10/1989 |
| EP | 1 069 183 | A2 | 1/2001 |
| EP | 1149849 | A1 | 10/2001 |
| EP | 1685855 | A1 | 8/2006 |
| JP | 7 079775 | A | 3/1995 |
| JP | 2000-505341 | A | 5/2000 |
| JP | 2001-207383 | A | 8/2001 |
| JP | 2001 340436 | A | 12/2001 |
| JP | 2004-026881 | A | 1/2004 |
| JP | 2005 131567 | A | 5/2005 |
| JP | 2006 006992 | A | 1/2006 |

(Continued)

OTHER PUBLICATIONS

Svensson et al. Aldehyde dismutase activity of human liver alcohol dehydrogenase. FEBS Letters 394 (1996) 217-220.*

(Continued)

*Primary Examiner* — Yong Pak
(74) *Attorney, Agent, or Firm* — Drinker Biddle & Reath LLP

(57) ABSTRACT

The invention relates to the use of an enzyme preparation which catalyzes the degradation of formaldehyde for reducing the formaldehyde content in a formaldehyde-containing formulation. In a preferred embodiment, the enzyme preparation contains a formaldehyde dismutase from a *Pseudomonas putida* strain. Further, the invention refers to a process for reducing the formaldehyde content in cross-linking agents for textile finishing or in polymer dispersions used, e.g. in construction chemistry. Further the invention relates to the use of an enzyme preparation which catalyzes the degradation of aldehydes for reducing the formaldehyde content in an aldehyde-containing formulation. Furthermore, the invention relates to a novel variant of the formaldehyde dismutase from *Pseudomonas putida*.

28 Claims, 9 Drawing Sheets

(56) References Cited

FOREIGN PATENT DOCUMENTS

| | | | |
|---|---|---|---|
| JP | 2009-019079 | A | 1/2009 |
| WO | WO-97/31682 | A1 | 9/1997 |
| WO | WO-98/29393 | A1 | 7/1998 |
| WO | WO-2005/046744 | A1 | 5/2005 |
| WO | WO-2009/013093 | A1 | 1/2009 |

OTHER PUBLICATIONS

Hoog et al. The gamma 1 and gamma 2 subunits of human liver alcohol dehydrogenase. cDNA structures, two amino acid replacements, and compatibility with changes in the enzymatic properties. Eur. J. Biochem. 159 (2), 1986.*

Hoog et al. Structure of the class II enzyme of human liver alcohol dehydrogenase: combined cDNA and protein sequence determination of the pi subunit. Biochemistry 26 (7), 1926-1932 (1987).*

Branden et al. Introduction to Protein Structure, Garland Publishing Inc., New York, p. 247, 1991.*

Adroer, N., et al., "Mechanism of Formaldehyde Biodegradation by *Pseudomonas putida*", Appl. Microbiology and Biotechnoloy, vol. 33, (1990), pp. 217-220.

Fujii, Y., et al., "The Artificual Evolution of an Enzyme by Random Mutagenesis: The Development of Formaldehyde Dehydrogenase", Bioscience Biotechnology and Biochemistry, vol. 68, No. 8, (2004), pp. 1722-1727.

Hasegawa, T., et al., "The X-Ray Crystal Structure of Formaldehyde Dismutase at 2.3A Resolution", Acta Cryst., vol. A 58 (Supplement), (2002), pp. C102.

Kato, N., et al., "The Dismutation of Aldehydes by a Bacterial Enzyme", Agric. Biol. Chem., vol. 47, No. 1, (1983), pp. 39-46.

Tanaka, N., et al., "Crystal Structure of Formaldehyde Dehydrogenase from *Pseudomonas putida*: The Structural Origin of the Tightly Bound Cofactor in Nicotinoprotein Dehydrogenases", Journal of Molecular Biology, vol. 324, No. 3, (2002), pp. 519-533.

Tomasino, C., et al., "Evalution of Formaldehyde Scavengers", Durable Press Finishing, Textile Chemist and Colorist, vol. 16, No. 12, (1984), pp. 33-38.

Yanase, H., et al., "Cloning, Sequence Analysis, and Expression of the Gene Encoding Formaldehyde Dismutase from *Pseudomonas putida* F61", Bioscience Biotechnology Biochemistry, vol. 59, No. 2, (1995), pp. 197-202.

Yanase, H., et al., "Effects of GroESL Coexpression on the Folding of Nicotinoprotein Formaldehyde Dismutase from *Pseudomonas putida* F61", Bioscience Biotechnology and Biochemistry, vol. 66, No. 1, (2002), pp. 85-91.

Database WPI, Thomson Scientific, XP002535423, JP 2005 131567A (2005).

Database WPI, Thomson Scientific, XP002535424, JP 2006 006992 A (2006).

Database WPI, Thomson Scientific, XP002535425, JP 2001 340436 A (2001).

Database WPI, Thomson Scientific, XP002535426, JP 7 079775 A (1995).

Annex to Form PCT/ISA/206, Communication Relating to the Results of the partial International Search, PCT/EP2010/054284 dated Oct. 11, 2011.

International Preliminary Report on Patentability for International Application No. PCT/EP2010/054284 dated Oct. 11, 2011.

English Translation of Japanese Office Action Application No. 2012-503977 dated Aug. 19, 2014.

* cited by examiner (A)

(B)

(C)

USE OF ENZYMES TO REDUCE ALDEHYDES FROM ALDEHYDE-CONTAINING PRODUCTS

RELATED APPLICATIONS

This application is a United States national stage application under 35 U.S.C. § 371 of PCT/EP2010/054284, filed Mar. 31, 2010, which claims benefit of European application 09157522.5, filed Apr. 7, 2009.

SEQUENCE LISTING

The Sequence Listing associated with this application is filed in electronic format via EFS-Web and is hereby incorporated by reference into the specification. The name of the text file containing the Sequence Listing is REPLACEMENT_SEQ_LIST_12810-01267-US _ST25.txt. The size of the text file is 42 KB, and the text file was created on Sept. 30, 2011.

FIELD OF THE INVENTION

The present invention relates to the enzymatic removal of formaldehyde from formulations containing formaldehyde and from products treated with said formulations.

BACKGROUND OF THE INVENTION

Formaldehyde (for the purposes of convenience hereinafter often referred to as "FA") is an important chemical used widely by industry to manufacture building materials and numerous household products. FA is used for example for crease-resistant finishing in the textile industry, for the production and coating of chipboards in the wood processing industry, and for the production of synthetic resins like phenolic plastics or aminoplasts in the chemical industry. Due to its high volatility FA is released into the air during the production processes and is considered as an important impact on health and environment.

FA has four basic uses: as an intermediate in the production of resins; as intermediate in the production of industrial chemicals; as a biocide; and as a component in the formulation of end-use consumer items. The manufacture of resins accounts for about 65 percent of total consumption. About one-third is used in the synthesis of high volume chemical derivatives, including pentaerythritol, hexamethylenetetramine, and butanediol. Two percent is used in textile treating and small amounts of FA are present as preservatives or bioicides in consumer and industrial products, such as cosmetics, shampoos and glues. The largest amounts of FA are used for producing condensates (i.e. resins) with urea, melamine, naphthaline sulfonate, and phenol and, to a small extent, with their derivatives. The main part of these resins is used for the production of adhesives and impregnating resins, which are employed for manufacturing particle boards, plywood, and furniture. These condensates are also employed for the production of curable molding materials; as raw materials for surface coating and as controlled-release nitrogen fertilizers. They are used as auxiliaries in the textile, leather, rubber, and cement industries. Further uses include binders for foundry sand, rockwool and glasswool mats in insulating materials, abrasive paper, and brake linings. Very small amounts of urea-FA condensates are used in the manufacture of foamed resins that have applications in the mining sector and in the insulation of buildings and transportation vehicles.

Some products based on FA contain unreacted FA in excess which may be released from the product or released through subsequent hydrolysis. One example is urea-FA resin. Urea-FA resin is a generic name that actually represents an entire class of related formulations. About 60 percent of urea-FA resin production is consumed by particleboard and plywood manufacturing, where the resin is used as glue. Urea-FA resins are also used in decorative laminates, textiles, paper, and foundry sand molds.

Finally, FA resins are used to treat textiles to impart wrinkle-resistance to clothing. Resin or chemical finishing is in most cases the last stage of modern textile production. The goal is to convert the bleached, dyed or printed fabric by mechanical and chemical treatment into suitable state for sale. One of the most important processes is the washfast finishing of woven and knitted fabrics composed of cotton, other cellulosic fibres, and their blends with synthetic fibres.

Initially, resin-finishing agents were developed to improve the shrinkage of viscose staple fabrics. These compounds were usually derived from formaldehyde and urea. In order to improve the competitiveness of cotton on the textile market, heterocyclic cross-linking reagents based on formaldehyde, urea and glyoxal have been developed and are commonly used for easy-care and wrinkle-free finishing. Due to the suspected harm in humans, FA levels in products and industrial processes have to be kept as low as possible.

The prior art discloses various technologies for the purpose of removing FA, e.g. air-borne when released from products or directly from well-known and widely used resins as introduced supra. U.S. Pat. No. 5,352,274 discloses air filtration utilizing a plurality of corrugated base sheets which are stacked or nestled and which have entrapped carbon dust for adsorption of impurities such as FA, acetaldehyde, and acrolein. This technology provides a method to adsorb FA molecules physically but not degradation by a chemical or biochemical reaction. U.S. Pat. No. 5,830,414 discloses the treatment of carbon fibers with an active small molecule such as a strong acid, strong base, or strong oxidizing agent. These chemicals can only be used to treat fibers having high chemical resistances such as activated carbon fibers. Further, fibers thus treated are potentially hazardous to handle. The use of formaldehyde degrading enzymes in air filters is described in JP2001340436.

With respect to textile industry and building materials, FA reducing agents should not adversely affect fabric properties such as hand, shrinkage, strength retention and shade or whiteness or the mechanical properties of the particleboard. And, of course, it must be economical to use in production and efficient at reasonable levels. In the textile industry, compounds having active methylene groups have been used as FA reducing agents to reduce the amount of FA released from durable press-treated fabrics as described in Textile Chemist and Colorist, Vol. 16, No. 12, p. 33, December 1984 (published by the American Association of Textile Chemists and Colorists). FA reducing agents containing active methylene hydrogens also may be added to coating compositions containing urea/formaldehyde or melamine/formaldehyde resin to reduce formaldehyde concentration (e.g. described in U.S. Pat. No. 5,795,933). Also the addition of urea and its derivatives is known to scavenge formaldehyde.

The prior art has not disclosed FA reducing agents which are effective in reducing released FA to the low levels which are currently desired without detrimental effects on the properties of the materials to be treated with said resins. Currently, the FA reducing agents most widely used in durable press finishing compositions are polyhydric alcohols, such as diethylene glycol and sorbitol and in the manufacture of particleboard nitrogen containing compounds such as urea, melamine, diazine, triazine and amine compounds (U.S. Pat. No. 4,559,097). Compounds such as these, however, are not sufficiently effective in reducing FA levels to produce the low levels which are currently desired. Moreover, they only bind FA and do not catalyze its degradation. Also some formaldehyde scavengers like urea slow down reactivity of textile cross-linkers, reducing their efficiency.

Formaldehyde Dismutase (hereinafter referred to as "FDM") activity has been first described by Kato and co-workers in 1983 (Kato et al., 1983, Agric. Biol. Chem., 47(1), pages 39-46) but no corresponding gene has been identified until 1995 (Yanase et al. 1995, Biosci. Biotechnol. Biochem., 59(2), 197-202). The first protocol for recombinant production and purification of soluble FDM has been published in 2002 (Yanase et al. 2002, Biosci. Biotechnol. Biochem., 66(1), 85-91). A crystal structure for FDM (Hasegawa et al. 2002, Acta Crystallogr., Sect. A, 58, C102-C102) and other related enzymes are available since 2002 (Tanaka et al. 2002, Journal of Molecular Biology, 324, 519-533).

SUMMARY OF THE INVENTION

Accordingly, the technical problem underlying the present invention is to provide efficient methods and means to reduce the FA content from formulations that are used to treat various materials, e.g. in textile or construction industry, overcoming the disadvantages of the prior art. The problem is solved by the subject-matter of the present invention, namely, the inventors have surprisingly found that the formaldehyde content in resins that are used to treat such materials, can be efficiently reduced by using an enzyme that catalyzes the degradation of formaldehyde.

Furthermore, the present invention describes the design, characterization and crystal structures of FDM mutants with improved specificity towards formaldehyde, enhanced activity towards acetaldehyde, and increased thermostability. Particularly, the FDM $I^{301}L$ mutant shows increased activity on formaldehyde compared to the wild-type protein and is more thermostable. This enzyme can be easily produced in high yield by fermentation and formulated as a spray-dried powder.

Thus, an object of the invention relates to the use of an enzyme preparation which catalyzes the degradation of formaldehyde for reducing the formaldehyde content in a formaldehyde-containing formulation.

In a preferred embodiment, the enzyme preparation contains an enzyme which comprises the amino acid sequence of SEQ ID NO:2 or variants thereof. In a further embodiment, the enzyme is a formaldehyde dismutase (FDM) from a bacterial strain, preferably of the E.C classification EC 1.2.99.4. or EC 1.2.1.46., which is derived from a *Pseudomonas putida* strain.

In a particularly preferred embodiment, the enzyme preparation contains an enzyme which comprises the amino acid sequence of SEQ ID NO: 8, or SEQ ID NO: 10.

In a further preferred embodiment, the formulation is a resin. The resin can be a cross-linking agent for textile fabrics or a polymeric dispersant, employed to generate polymer dispersions. In a preferred embodiment the cross-linking agent is used for textile fabrics that contain cellulosic fibers such as cotton or viscose or a mixture thereof and blends with synthetics.

The resulting polymer dispersions are suitable for treating materials e.g. such as building or construction materials, leather and hides, fiberboard, particle board, plywood and/or carpeting, and suitable for coating applications or paper making.

In another embodiment, the invention refers to a process for reducing the formaldehyde content in a formaldehyde-containing formulation comprising contacting the formulation with an enzyme preparation that catalyzes the degradation of formaldehyde.

The invention relates also to a process for reducing the formaldehyde content in a textile fabric, comprising contacting the textile fabric with an enzyme preparation which catalyzes the degradation of formaldehyde. Furthermore, it relates to formulations comprising a cross-linking agent for textiles or a polymeric dispersant and an enzyme preparation which catalyzes the degradation of formaldehyde.

Other embodiments of the invention relate to a codon-optimized, dismutase-encoding nucleic acid, vectors containing said nucleic acid, and expression host.

Furthermore the invention relates to isolated nucleic acid encoding novel FDM variants, the amino acid sequence of said FDM variants, as well as the particular uses thereof.

DESCRIPTION OF THE SEQUENCES

SEQ ID NO:1

Figure 1:
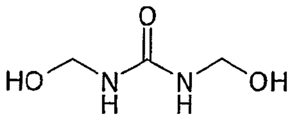
FIG. 1: A few formaldehyde-based cross-linking reagents. (A) urea-FA, (B) melamine-FA, (C) dimethyloldihydroxyethylene urea (DMDHEU).
Figure 1:
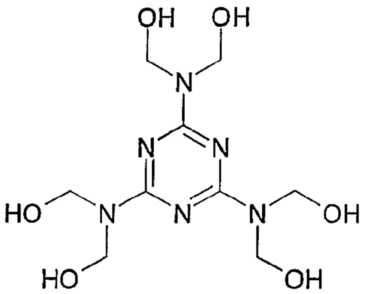
Figure 1:
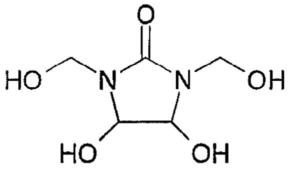

Nucleic acid sequence of formaldehyde dismutase, genebank accession number L25862 (CDS 323 . . . 1522)

SEQ ID NO:2

Protein sequence of formaldehyde dismutase, genebank accession number L25862

SEQ ID NO:3

Optimized DNA sequence for FDM from *Pseudomonas putida* F61 (1197 bp)

SEQ ID NO:4

Nucleotide sequence of pDHE-FDM

SEQ ID NO:5

Nucleotide sequence of pAgro

SEQ ID NO:6

Nucleotide sequence of pHSG

SEQ ID NO:7

Nucleic acid sequence of formaldehyde dismutase Ile-301-Leu

SEQ ID NO:8

Protein sequence of formaldehyde dismutase Ile-301-Leu

SEQ ID NO:9

Nucleic acid sequence of formaldehyde dismutase Phe-93-Ala/Ile-301-Leu

SEQ ID NO:10

Protein sequence of formaldehyde dismutase Phe-93-Ala/Ile-301-Leu

DEFINITIONS

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention, which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list.

The term "formaldehyde" or "FA" refers to a compound of the general formula $CH_2O$, having the CAS number 50-00-0. It also known to the skilled artisan as formalin, methylene oxide, methyl aldehyde, methanal, HCHO, formic aldehyde, oxomethane, formol, oxymethylene, morbicid, veracur, methylene glycol, formalin 40, BFV, fannoform, formalith, FYDE, HOCH, karsan, lysoform, superlysoform, methan 21. In pure form, formaldehyde is a gas but is often used in liquid form after diluting with water as the hydrate $HO—(CH_2O)_n—H$ known as methandiol. Aqueous solutions of formaldehyde are referred to as formalin. It is a colorless highly flammable liquid or gas with a pungent odor that is detectable at 1 part per million (ppm). Formaldehyde mixtures (e.g. mixtures with water, acetone, benzene, diethyl ether, chloroform and ethanol) are included for the purposes of the present invention as well. Polymers of formaldehyde encompassed in the present definition include low and high molecular mass polymers, in particular paraformaldehyde, as well as linear and cyclic polyoxymethylenes The term "acetaldehyde" or "AA" refers to a compound of the general formula $CH_3CHO$ having the CAS number 75-07-0. It is also known to the skilled artisan as ethanal and is a colorless liquid with a pungent, suffocating odor that is slightly fruity when diluted. Acetaldehyde is an intermediate in the metabolism of plant and animal organisms, in which it can be detected in small amounts. Larger amounts of acetaldehyde interfere with biological processes. As an intermediate in alcoholic fermentation processes it is present in small amounts in all alcoholic beverages, such as beer, wine, and spirits. Acetaldehyde also has been detected in plant juices and essential oils, roasted coffee, and tobacco smoke. At higher concentrations (up to 1000 ppm), acetaldehyde irritates the mucous membranes. The perception limit of acetaldehyde in air is in the range between 0.07 and 0.25 ppm. At such concentrations the fruity odor of acetaldehyde is apparent. Conjunctival irritations have been observed after a 15-min exposure to concentrations of 25 and 50 ppm, but transient conjunctivitis and irritation of the respiratory tract have been reported after exposure to 200 ppm acetaldehyde for 15 min.

The term "methylglyoxal" refers to a compound of the general formula ($CH_3—CO—CH{=}O$), having the CAS number 78-98-8 (Kato et al., 1983, Agric. Biol. Chem., 47(1), pages 39-46). It also known to the skilled artisan as pyruvaldehyde, 2-oxopopanal, 2-oxopropionaldehyde, and is formed as a side product of several metabolic pathways.

"Formulation", as used herein, means a chemical composition, manufactured according to a specific formula and/or recipe. It is, thus, distinguished from naturally occurring FA-containing sources. The formulation is manufactured by employing the addition of FA. In some instances, the formulation is also referred to as "FA condensate".

As used herein, the phrase "resin" means a low molecular weight substance that will subsequently be reacted to form a high molecular weight polymer or to crosslink functional polymer chains like cellulose. Particularly the term resin refers to "synthetic resins" which are defined as resins resulting from controlled chemical reactions such as polyaddition or polycondensation between well-defined reactants including formaldehyde that do not themselves have the characteristics of resins. Synthetic resins can mean also resins obtained by polymerization of unsaturated monomers. This term includes (i) Hydrocarbon resins, i.e., synthetic resins from coal tar, petroleum, and turpentine streams, produced by polymerization. These resins are used like natural ones, e.g., in combination with other polymers to impart special properties such as tack, flow, and hardness to a material, and (ii) Synthetic resins obtained mainly by addition polymerization and polycondensation in the presence of formaldehyde, which are intermediates in the synthesis of higher molecular mass plastics. Examples and preferred embodiments of such resins are disclosed in greater detail hereinafter.

As used herein, the term "enzyme preparation" is intended to cover any preparation of enzyme (howsoever obtained) at any level of purity (including using the host expressing the enzyme, i.e. *E. coli*), as long as the preparation is enzymatically active. The enzyme preparations of the invention include preparations exhibiting a plurality of different specific activities, and are conveniently used in the form of more or less crude enzyme extracts in admixture with one or more carriers.

As used herein, the term "cross-linking agent" or "crosslinker" means a FA-containing resin, as defined supra, which can be used to cross-link cellulose molecules in textile fabrics for imparting wrinkle resistance and durable press properties, particularly to cellulosic textiles. Examples and preferred embodiments of such cross-linking agents are disclosed in greater detail hereinafter.

The term "textile fabric" or "fabric" as used herein means products and objects made from natural textile fabrics such as jute, sisal, ramie, hemp, and cotton as well as many of the synthetic fibers, such as viscose, rayon, cellulose esters, vinyl resin fibers, polyacrylonitrile and copolymers thereof, polymers and copolymers of olefins such as ethylene, polyimide or nylon types, polyester and the like. The fabrics used can be those of a single composition or a mixture of fibers.

The term "polymeric dispersants" refers to polyelectrolytes that are readily soluble in water. The most common representatives are alkali-metal polycarbonates, polysulfonates, or polyphosphates, usually sodium salts. Preferred dispersants are produced by condensation of aromatic compounds with formaldehyde. The use of condensation products of aromatic sulfonic acid with formaldehyde is very widespread. Typically those are either anionic formaldehyde resins based on naphthalinsulfonate, melamine sulfonate or phenol or derivatives thereof. Other polymeric dispersants include graft polymers based on anionic backbones and nonionic side chains. As such typically polycarboxylates are used as backbones and polyalkylenglykols are used as sidechains. Said polymeric dispersants allow reducing the water content in hydraulic binder mixtures as cement and calcium sulfate based systems, without a reduction in workability, rheological properties respectively. They further can be used to improve the workability of hydraulic binders or to increase the strength development. Polymeric dispersants are also known in the art as "superplasticizers". Such polymeric dispersants are also used in textile dying liquors in order to stabilize dye dispersions.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence of SEQ ID NO:1. By "variant" polypeptide is intended a polypeptide derived from the protein of SEQ ID NO:2 by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

"Sequence identity" refers to the extent to which two optimally aligned DNA or amino acid sequences are invariant throughout a window of alignment of components, e.g., nucleotides or amino acids. An "identity fraction" for aligned segments of a test sequence and a reference sequence is the number of identical components that are shared by the two aligned sequences divided by the total number of components in reference sequence segment, i.e., the entire reference sequence or a smaller defined part of the reference sequence. "Percent identity" is the identity fraction times 100. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc. Burlington, Mass.).

The term "ppm" (parts per million) refers to mass shares and is equivalent to "mg/kg".

Polypeptide(s)/Protein(s)

The terms "polypeptide" and "protein" are used interchangeably herein and refer to amino acids in a polymeric form of any length, linked together by peptide bonds.

Polynucleotide(s)/Nucleic Acid(s)/Nucleic Acid Sequence(s)/Nucleotide Sequence(s)

The terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

Homologue(s)

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds).

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Derivatives

"Derivatives" include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

DETAILED DESCRIPTION OF THE INVENTION

The present invention relates to the use of an enzyme preparation which catalyzes the degradation of formaldehyde for reducing the formaldehyde content in a formaldehyde-containing formulation.

Enzymes that catalyze the degradation of formaldehyde are known in the art. For example, Bystrykh et al. (1993) J. Gen. Microbiol. 139, 1979-1985; Sakai, Y. et al (1995) FEMS Microbiol. Lett. 127, 229-234; or Ito et al. (1994) J. Bacteriol. 176, 2483-2491 or Gonzalez et al., J. Biol. Chem., Vol. 281, NO. 20, pp. 14514-14522, May 19, 2006 describe enzymes like S-formylglutathione hydrolase, formaldehyde dismutase, methylformate synthase, or glutathione-independent formaldehyde dehydrogenase, which can be employed for degradation of FA.

Enzymes belonging to the zinc-containing medium-chain alcohol dehydrogenase family are particularly suitable for the present invention (see also Tanaka et al., J. Mol. Biol. (2002) 324, 519-533). In a preferred embodiment, the pyridine nucleotide NAD(H), which is distinct from the co-enzyme (as cosubstrate) in typical alcohol dehydrogenases, is tightly but not covalently bound to the enzyme and acts as a cofactor.

"Tightly bound" means that the cofactor is bound to the enzyme by interactions such as ionic bonds, intermolecular forces, hydrogen bonds, van der Waal's forces, hydrophobic interactions. Since the cofactor is being recycled during the disproportionation reaction (reduction of FA to methanol and oxidation of FA to formic acid by the same enzyme), the process of the present invention bears the particular advantage of minimizing costs, because the cofactor does not have to be provided continuously to the reaction mixture, in order to maintain the enzyme activity.

Particularly suitable for the use of the present invention are oxidoreductases that are acting on the aldehyde or oxo group of donors (E.C. class 1.2.). Preferred are oxidoreductases with acceptors other than NAD or NADP, cytochrome, oxygen, a disulfide, an iron-sulfur protein (E.C. class 1.2.99). Preferably, the enzyme is a formaldehyde dismutase (hereinafter often abbreviated as "FDM") from a bacterial strain, more preferably of the E.C classification EC 1.2.99.4. or EC 1.2.1.46., which is derived from a *Pseudomonas putida* strain. Said enzyme is further described in Kato, N., et al. (1983) Agric. Biol. Chem., 47(1), 39-46, Yanase, H., et al. (1995) Biosci. Biotechnol. Biochem., 59(2), 197-202 and Yanase, H., et al. (2002) Biosci. Biotechnol. Biochem., 66(1), 85-91.

In a preferred embodiment, the enzyme preparation contains an enzyme which comprises the amino acid sequence of SEQ ID NO:2 or variants thereof. In a further preferred embodiment, the enzyme preparation contains an enzyme encoded by the nucleic acid of SEQ ID NO:1, or variants thereof.

In a particularly preferred embodiment, the enzyme preparation contains an enzyme which comprises a variant or derivative of the amino acid sequence of SEQ ID NO:2, as described in more detail hereinafter, wherein the phenylalanine at position 93 and/or the isoleucine at position 301, and/or the methionine at position 337 and/or the phenylalanine at position 127 have been substituted by any other amino acid.

For the use of the present invention, the enzyme preparation can be used either purified having various levels of purity or as unpurified extract, for example as bacterial extract, i.e. extract from the bacteria which naturally produce the desired enzyme or bacteria which are used as expression hosts. Alternatively, it is also possible to use growing cells which comprise FDM encoding nucleic acids, nucleic acid constructs or vectors bearing said nucleic acids, without including any protein purification step. It is also possible to use quiescent or disrupted cells. Disrupted cells are understood to mean, for example, cells which have been made permeable by means of a treatment with, for example, solvents, or cells which have been disrupted by means of an enzyme treatment, by means of a mechanical treatment (for example French Press or ultrasound) or by means of another method. The crude extracts thus obtained are suitable in an advantageous manner for the use according to the invention. It is also possible to use purified or partly purified enzymes for the process. Immobilized microorganisms or enzymes, which can advantageously find use in the reaction, are likewise suitable. When free organisms or enzymes are used for the process according to the invention, they are appropriately removed before the extraction, for example by means of a filtration or centrifugation.

Depending on the FA-containing formulation to be contacted, the enzyme preparation may be employed in a free (soluble or solid) or immobilized form. An immobilized enzyme means an enzyme which is fixed to an inert support. Suitable support materials and the enzymes immobilized thereon are disclosed in EP-A-1149849, EP-A-1 069 183 and DE-A 100193773 and in the references cited therein. On this matter, reference is made to the disclosure of these publications in their entirety. Examples of suitable support materials are clays, clay minerals such as kaolinite, diatomaceous earth, perlite, silicon dioxide, aluminum oxide, sodium carbonate, calcium carbonate, cellulose powder, anion exchanger materials, synthetic polymers such as polystyrene, acrylic resins, phenol-formaldehyde resins, polyurethanes and polyolefins such as polyethylene and polypropylene. The support materials are usually employed in a finely divided, particulate form for preparing the supported enzymes, with preference being given to porous forms. The particle size of the support material is usually no more than 5 mm, in particular no more than 2 mm (sieve grade). Analogously, when using the FDM as whole cell catalyst, a free or immobilized form may be chosen. Examples of support materials are calcium alginate and carrageenan. Enzymes as well as cells may also be linked directly with glutaraldehyde (crosslinking to give CLEAs). Corresponding and other immobilization processes are described, for example, in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim.

The amount of enzyme to be used depends on the purity level of the enzyme preparation. Typical amounts for the process of the present invention ranges between 0.1 to 1000 units per gram of treated FA-containing formulation, preferably between 1 to 500 units, more preferably between 5 to 100 units, even more preferably between 8 to 30 units, most preferably between 9 to 15 Units per gram of treated FA-containing formulation. One Unit is defined as the amount of enzyme necessary to catalyze the formation of 1 μmol formic acid per minute. Purified FDM has a specific activity of about 100-200 U/mg. Enzyme amounts are merely approximate values that may vary depending on the reaction conditions like temperature and incubation period. The optimal enzyme amount can easily be determined by performing routine experiments.

The present invention can be applied to all formulations which have been furnished with formaldehyde. The largest group of formaldehyde-containing formulations is the group of resins containing urea, melamine, naphthaline and phenol and their derivatives like DMDHEU. Spray drying additives and rheology modifiers used in the production of dispersions like polycondensates of FA with phenol sulfonic acid or naphthalene sulfonic acid. Other formulations include binders for foundry sand, rockwool and glasswool mats in insulating materials, abrasive paper, and brake linings or urea-formaldehyde condensates that are used in the manufacture of foamed resins. Other formulations containing formaldehyde include pentaerythritol (employed chiefly in raw materials for surface coatings and in permissible explosives) and hexamethylenetetramine used as a cross-linking agent for phenol-formaldehyde condensates and permissible explosives. In the cosmetics industry, formaldehyde is employed as a preservative in hundreds of products, for example, soaps, deodorants, shampoos, and nail-hardening preparations. Formaldehyde solutions are also known in the art to be used as a preservative for tanning liquors, dispersions, crop protection agents, and wood preservatives. Furthermore, formaldehyde is required in the sugar industry to prevent bacterial growth during syrup recovery.

Accordingly, in a preferred embodiment, the formaldehyde-containing formulation to be contacted with an enzyme preparation which catalyzes the degradation of formaldehyde is a resin. A general definition of a resin, in particular synthetic resins, is given supra.

Preferably, the present invention can be applied to FA resins which are obtained by addition polymerization and polycondensation. Examples include furan resins, ketone and aldehyde resins, such as acetophenone formaldehyde resins or acetone formaldehyde resins, phenol resins such as novolacs and resols, epoxy resins such as liquid epoxy resins (DGEBA), solid epoxy resins based on DGEBA, halogenated epoxy resins epoxy novolac resins, sulfonamide resins or aniline resins.

For example, phenol resins which are widely employed for gluing woods are condensates of different phenolic compounds and aldehydes. The phenolic compound can be phenol itself, polyhydric phenols, and aliphatically or aromatically substituted phenols. Examples of phenolic compounds are alkyl phenols such as resorcinol, alkyl resorcinol, cresols, ethyl phenol and xylenol, and also phenolic compounds of natural origin such as tannins, cardenol, and cardol. Formaldehyde based phenol resins in the phenol resin composition include resorcinol-formaldehyde, phenol-resorcinol-formaldehyde, and tannin-formaldehyde resins.

In a particularly preferred embodiment, the FA resin is an amino resin, such as urea resin, urethane resin, melamine resin, cyanamide and dicyanodiamide resin Amino resins are commonly used as adhesives; impregnating resins; molding materials; starting materials for making surface coatings; auxiliaries for paper, textiles, leather, and flotation; strengtheners for building materials; superplasticizers; binders for glass fibers and foundry sand casting; fire lighters; emery papers; flame retardant coatings; flame-proofed combustible items; foamed resins for many purposes; grinding wheels; ion-exchange resins; sewage flocculants; and microcapsule production.

As used herein, the phrase "adhesive" means a glue to hold materials together, a laminating resin and a matrix resin to hold materials together. Glues and impregnating resins are aqueous adhesives made from urea, melamine and/or phenol with formaldehyde. Glues are known in the art for the manufacturing of wood based panels like e.g. particle board, medium density fibre-board MDF, oriented strand board OSB, plywood, core board or sheeting. Impregnating resins are used for impregnating papers, which are used for the decorative coating of wood based panels, e.g. on the surface of furniture and laminate flooring. Impregnating resins are used as resin glues in the particle board, plywood, fiberboard, and furniture industries. Impregnating resins also are used to impregnate papers for decorative laminates and for coating wood particle board.

Textile materials are presently generally rendered wrinkle resistant or non-iron in a process known as pad-dry-cure process, generally to crosslink the cellulose molecules. Such cross-linking of the cellulose imparts to the fabric a tendency to return to its original shape and smoothness. Some classes of DMDHEU resins, as described supra, have been extensively used in the past as the cross-linking agents in such a process.

Accordingly, in another embodiment of the present invention, the crosslinker to be contacted with an enzyme preparation which catalyzes the degradation of formaldehyde is a cross-linking agent suitable for finishing textile fabrics.

Cross-linking agents used in the textile-finishing industry have been widely described in the art (See, for example, Ullmann IVth Edition Vol 23). Cross-linking agents which are known to the person skilled in the art include "self-crosslinking" (having a reactive hydrogen atom on the nitrogen atom) and "reactant crosslinking" agents (nitrogen is part of a heterocyclic ring).

Multifunctional methylol derivatives of urea, substituted ureas, or melamine produced by reacting formaldehyde for with these compounds are preferred cross-linking agents for commercial easy care finishes. An important group is constituted by hydroxymethyl compounds of cyclic urea derivatives; examples are dihydroxymethylethylene urea, dihydroxymethylpropylene urea, and dihydroxymethylurone. Acyclic compounds, such as various alkyl carbamates, are also typical finishing agents. In contrast to the pure urea-formaldehyde compounds, these exhibit little tendency to form self-cross-linked resins and react predominantly with cellulose to cross-link the fibers.

The methylol derivatives of urea itself are used particularly on rayon fabrics. Examples include dimethylol urea, N,N"-bis(hydroxymethyl)urea, dimethyl ether of trimethylolmelamine, urons, i.e., tetrahydro-3,5-bis(hydroxymethyl)-4H-1,3,5-oxadiazin-4-one, cyclic urea products, methylol derivatives of carbamates, especially methyl carbamate, and methoxyethyl carbamate, Preferably, methylol derivatives of dihydroxyethylene urea, produced by reacting glyoxal with urea, are used as cross-linkers in easy care finishes, e.g. dimethylol dihydroxyethylene ureas (DMDHEU), described for example in WO98/029393, 1,3-dimethoxymethyl DHEU and the fully methylated product. All of the various modifications of the glyoxal-urea type products are in commercial use. The products which have been both methylated and contain a hydroxy compound afford the lowest formaldehyde evolution potential of all commercially available easy care finishes of the methylol type. A variety of crosslinkers is described in Ullmann IV.th Edition Vol 23 Chap 7.

Since the described cross-linking agents are predominantly used to cross-link cellulose molecules, the textile fabrics to be treated preferably contain cellulose or cellulosic fibers.

The present invention is suited to treating fibrous cellulosic material containing at least 10%, preferably at least 20%, at least 30%, at least 40%, at least 50%, at least 60%, at least 70%, at least 80%, at least 90%, most preferably up to 100% of cellulosic fibers. Examples include jute, linen, flax, hemp, viscose, regenerated cellulose such as rayon, and, preferably cotton. The cellulosic material may be woven, non-woven or knit or in the form of fibers, linters, rovings, slivers, scrims or papers. The fibrous cellulosic material may consist entirely of cotton or cotton blended with a synthetic fiber such as polyester or nylon.

As described supra, resins, particularly melamine resins, or any other amino-s-triazine such as guanamines, are widely used as building materials or superplasticizers (also known as concrete liquefiers). For these purposes, said resins are usually modified by reaction with other compounds. Especially useful are condensation products based on melamine, formaldehyde and sulfite (see for example EP 0 336 165).

These polymers may be conventionally prepared as dispersions by emulsion polymerization, initiated by polymeric dispersants, as defined in the definition section, in the presence of radical initiators, emulsifiers and/or protective colloids, where called for regulators and other additives.

Accordingly, in a further preferred embodiment of the present invention, the resin is a FA-containing polymeric dispersant or FA-condensate which is used to prepare polymer dispersions.

The term "polymer dispersion" refers to raw materials for the construction chemicals sector. Products include acrylic-dispersions as well as acrylic-powders and styrene/butadiene-dispersions. They enhance workability and technical performance of construction chemicals, building adhesives and sealants. High-class polymer dispersions and additives are used as architectural coatings raw materials in combination with other components to produce ready-to-use products such as paints, wood stains or texture finishes. In particular, the term is referred to dispersions containing methacrylic acid (MAS), methylolmethacrylamide (MAMol) and/or methylolacrylamide (AMol), homo- and copolymers of acrylamide, acrylic acid, acrylonitrile, acrylic acid esters and styrene also used as binders in textile pigment printing and/or coating. Further examples and preferred embodiments of such polymer dispersions are disclosed hereinafter.

The term "pigment printing" refers to processes for the coloristic patterning of sheetlike textile material which are common knowledge in the art and which have long been practiced all over the world. In pigment printing, the particular pigments are usually applied to the textile web from aqueous print pastes together with a binder system and then dried. A subsequent dry heat treatment for curing the preferably synthetic resin binder system and hence fixing the applied colorant concludes the printing process.

Furthermore, for use as building materials, the condensation products, such as sulfite-modified melamine resins, naphthaline sulfonates are combined with water-soluble vinyl- or acryl-based polymers. Examples of appropriate polymers are products of vinylacetate, vinylpropionate, vinyllaurate, vinylchloride, vinylidenechloride, straight-chain or branched vinylesters with 3 to 18 C atoms, poly(vinyl alcohol), poly(vinyl sulfates), acryl- and methacryl-monomers, in particular esters, also styrene and ethane, maleic acid-styrene copolymers which may be present in the form of their homo-, co-, ter-polymers and as graft polymers.

The preferred fields of application of such polymer dispersions are paints, decorative and protective coatings and lacquers, building chemicals, as additives in cement mortars and filling compounds, auxiliary materials for the manufacture of paper and paper coatings, textile coating, and colorants for plastics.

Furthermore, the inventors of the present invention have established different methods to apply the enzyme preparation that catalyzes the degradation of FA depending on the application.

Accordingly, another object of the present invention relates to a process for reducing the formaldehyde content in a formaldehyde-containing formulation comprising contacting the formulation with an enzyme preparation that catalyzes the degradation of formaldehyde.

The "contacting" may occur prior or during the intended use of the formulation. Contacting can mean adding to and/or mixing if the FA containing formulation is liquid or applying to a surface, if the formulation is a rather viscous or solid material.

In one example, the enzyme preparation may be added directly to a urea-formaldehyde resin used in the manufacture of particleboard or diluted with water and sprayed on the surface of the board before it is pressed. The enzyme applied or added depends on the nature of the resin added to the particleboard and the curing conditions. However, the correct amount for any particular case may be determined by testing various amounts of enzyme and evaluating the amount of formaldehyde released by the board.

The inventors have also found that the formaldehyde-content can be reduced in textile fabrics when the enzyme preparation which catalyzes the degradation of formaldehyde is directly applied to the textile itself.

Accordingly, another object of the present invention refers to a process for reducing the formaldehyde content in a textile fabric, comprising contacting the textile fabric with an enzyme preparation which catalyzes the degradation of formaldehyde.

Preferably, the textile fabrics are "crosslinked fabrics" which have been imparted with crease and wrinkle resisting properties under both wet and dry conditions by heating, drying, and curing with a finishing agent such as glyoxal resin, formalin, ureaformaldehyde resin, dimethylolurea, dimethyl ether of ureaformaldehyde, melamine formaldehyde resins, cyclic ethylene urea formaldehyde resins, e.g. dimethylol urea, triazine-formaldehyde resins, triazone formaldehyde resins and the like as described supra.

Briefly, textile fabrics treated with a cross-linker as defined supra are impregnated with the enzyme preparation as described in the example section. The detection of residual FA after incubation with the enzyme preparation can be carried out with wet or dried textile fabrics. Preferably, it is performed with wet textile fabrics.

The FA-containing formulations referred to in the present invention exhibit a concentration of formaldehyde of about 1 to 50.000 ppm. Typical amounts are 10 to 5.000 ppm. The process of the present invention allows for a significant reduction of the formaldehyde content.

Suitably, the FA content is reduced by 10, 20, 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99%, and 100% as compared to formulations, end products which were not contacted with the enzyme preparation.

Methods to determine the residual FA content are well-known in the prior art. Formaldehyde can be quantitatively determined by either physical or chemical methods. Quantitative determination of pure aqueous solutions of formaldehyde can be carried out rapidly by measuring their specific gravity. Gas chromatography and high-pressure liquid chromatography (HPLC) can also be used for direct determination. The most important chemical methods for determining formaldehyde are summarized in H. Petersen, N. Petri, Melliand Textilber. 66 (1985) 217-222, 285-295, 363-369. The sodium sulfite method is most commonly used. It is based on the quantitative liberation of base produced when formaldehyde reacts with excess sodium sulfite. The stoichiometrically formed base is determined by titration with an acid. Formaldehyde in air can be determined down to concentrations in the $\mu L/m^3$ range with the aid of gas sampling apparatus. The quantitative determination of formaldehyde in air by the sulfite/pararosaniline method is described in Verein Deutscher Ingenieure (VDI): 1, Messen gasförmiger Immissionen, Bestimmen der Formaldehydkonzentration nach dem Sulfit-Pararosanilin-Verfahren, Richtlinie VDI 3484, Blatt 1, Düsseldorf 1979.

There are a number of further test methods that are used for the formaldehyde release analysis on textiles, such as Japanese Law112 (i.e. acetylacetone method), AATCC-112 (i.e. chromotropic acid method), the Shirley I and II Methods and others. Preferred methods for the detection of FA in textiles, are the LAW112 and the AATCC112 methods, used by the "European Committee for Standardization" in EN ISO 14184 part 1 and part 2. With the process of the present invention it is possible to reduce the residual formaldehyde content to less than 250, preferably less than 100, more preferably less that 50, even more preferably less than 20, and most preferably less than 10 ppm.

The temperature range needed to carry out the process of the present invention can vary between 10° C. to 100° C., preferably 20° C. to 40° C., more preferably 25° C. to 35° C., most preferred at 30° C. The process of the present invention is usually carried out under pH conditions varying between 3 and 12, preferably between 5 and 9, more preferably between 7 and 8. The optimal pH value can be determined and adjusted by means well-known to the person skilled in the art.

The incubation period can vary, depending on the chosen amount of enzyme, the reaction temperature and the FA content in the formulation, as well as depending on the nature of the formulation itself. Typically, the incubation period is in a range of minutes or hours, preferably 5 minutes to 10 hours, more preferably, 20 min to 5 hours, more preferably 30 min to 2 hours. The optimal incubation time can easily be determined and adjusted by the person skilled in the art depending on the product being treated.

The process of the present invention can be carried out batch-wise, semi-continuously or continuously in conventional bioreactors. Suitable regimes and bioreactors are familiar to the skilled worker and are described, for example, in Römpp Chemie Lexikon 9th edition, Thieme Verlag, entry header "Bioreactors" or Ullmann's Encyclopedia of Industrial Chemistry, 5th edition, volume B4, page 381ff, herein incorporated by reference. The operation of the reactor and the process regime can be adapted to the skilled artisan to the particular requirements of the desired FA degradation reaction. If the process is performed in batch mode the enzyme preparation is added directly after synthesis, polymerization, isolation, and, optionally, purification of the formulation. After successful formaldehyde degradation using FA dismutase the enzyme can be separated from the formulation. Alternatively, the enzyme can be left in the formulation and inactivated, e.g. by heat or acidification, if desired and provided such inactivation is not deleterious to the formulation. If the process is performed continuously the enzyme preparation is preferably immobilized on a carrier which can be packed, e.g., into a specific column. Typically, the formulation is the pumped over the column under suitable conditions. To further enhance the FA reducing effect, it is possible to serially connect several enzyme reactors one after the other.

For the purposes of the present invention, the enzyme preparation can be added in any form, formulation and composition known to the person skilled in the art. Those skilled in the art will readily appreciate that the enzyme preparation suitable for the present invention will be dependent on several factors, including but not limited to the precise composition of the FA-containing formulation. They will further appreciate that there are several methods for formulating enzyme preparations. The enzyme preparation may be formulated employing standard approaches of enzyme granule and/or liquid formulations. A description of the steps associated with enzyme granule and/or liquid formulation of enzymes is found in "Industrial Enzymes and their Application", by Helmut Uhlig, John Wiley and Sons, 1998

Suitable enzyme preparations are, for example, solid enzyme preparations obtainable by granulation, extrusion, spray drying, or lyophilization of enzyme solutions, as well as preferably concentrated solutions of the enzyme, optionally containing stabilizers. Alternatively, the enzyme preparation in solid or liquid form can be adsorbed on a solid carrier and/or being encapsulated. Methods that have been proposed for preparation of immobilized enzymes include the substrate-binding method, the cross-linking polymerization method, the gel-inclusion method, and the like.

In some embodiments, when the enzyme preparation used for the present invention is employed in a granular composition or liquid, it is desirable for the enzyme preparation to be in the form of an encapsulated particle to protect such enzyme from other components of the granular composition during storage. In addition, encapsulation is also a means of controlling the availability of the enzyme preparation during the FA degrading process and may enhance performance of the enzyme preparation. It is contemplated that any suitable encapsulating material will find use in the present invention. The encapsulating material typically encapsulates at least part of the enzyme preparation. Typically, the encapsulating material is water-soluble and/or water-dispersible. Briefly, the enzyme preparation is mixed with compounds such as sodium alginate, agarose or sephadex and subsequently precipitated according to methods known in the art. Alternatively, the encapsulation can be carried out by spray drying or extrusion of the enzyme preparation.

Examples of protective coating materials for said enzyme granules include natural materials such as saccharides, polysaccharides, polypeptides such as collagen, albumin or gelatine, oils, fatty acids, waxes. Also included as coating materials are semi-synthetic materials such as chemically modified cellulosic compounds, starch derivatives, or synthetic coating materials such as polyacrylates, polyamides. The coating can further comprise polyelectrolyte complexes that are generated by the interaction of polycations and polyanions. Typical polycations include natural compounds such as cytosan as well as synthetic polymers.

The enzyme preparation can be granulated together with a chemically inert carrier material or binding material. Carrier materials include silicates, carbonates or sulfates. Binding materials are for example non-crosslinked polymer compositions such as polyacrylate, polymethacrylate, polyvinylpyrrolidone, polysaccharides.

Alternatively, in order to protect the enzyme preparation against inactivation or denaturation, the addition of stabilizing compounds may be suitable. Examples for stabilizing compounds include protease inhibitors, such as boronic acid as well as derivatives thereof, amino alcohols, and low aliphatic alcohols. The enzyme preparations can be protected against physical effects or pH variations with compounds such as polyamid oligomers or polymeric compositions such as lignin, water-soluble vinyl copolymers. Furthermore, antioxidizing agents such as dithiothreitol (DTT) are typically used enzyme stabilizers.

If the enzyme preparation that catalyzes the degradation of formaldehyde shall be directly incorporated into the FA containing formulation, it is required in some embodiments that the enzyme is present in dried form. If the enzyme preparation that catalyzes the degradation of formaldehyde is added only during the application of the FA containing formulation, the enzyme preparation can be present in liquid, gelatinous, or paste-like form. Subsequent to protein purification and isolation methods well-known in the art the enzyme preparation can be added as concentrated aqueous solution, suspension or emulsion. Examples of solvents which can be used to obtain suitable enzyme preparations include alcohols, alkanolamines or glycol or glycol ethers, glycerol, sorbitol, glucose, saccharine. For the purposes of increasing the viscosity, the enzyme preparation can contain one or more thickener, also known as swelling agents. Suitable thickeners include, for example, alginates, pectins, starch, dextrine or synthetic thickener poly carbonic acids, polyethylene glycol, poly acryl compositions, polyamides, or polyethers.

For some formulations, it is desired that the enzyme preparation is already contained within the formulation keeping the FA content in these formulations as low as possible.

In a preferred embodiment, the enzyme preparation of the present invention comprises (a) 0.1-10% of an FA-degrading enzyme, preferably FDM, and (b) 1-80% of one or several polyols (glycol, glycerol, sorbitol, glucose, saccharose, polyethylene glycol etc.) and (c) 1-99% water.

In another embodiment of the invention, a dry (solid) enzyme preparation is added to a solid product formulation. The FA reducing activity is started upon addition of water to the solid preparation.

Therefore, another object of the present invention refers to a formulation suitable for textile-finishing, the formulation comprising a cross-linking agent and an enzyme preparation which catalyzes the degradation of formaldehyde.

The enzyme preparation may be used in a manner analogous to known formaldehyde-reducing agents. For example, the enzyme preparation may be incorporated into a durable press finishing cross-linking agent comprising an N-methyol cross-linking system, such as DMDHEU. A fabric composed either entirely or in part of cellulose fibers may be padded, foam finished or otherwise impregnated with the durable press finishing composition.

Preferably, the cross-linking agent is selected from the group consisting of melamine-FA, urea-FA or urea-glyoxal-FA compounds.

Another object of the present invention refers a formulation suitable for treating construction materials, particularly hydraulic binders such as cement, gypsum, mortar, or lean lime, fiberboard, particle board, plywood, wood, leather and/or carpeting, the formulation comprising a polymeric dispersant as described supra and an enzyme preparation which catalyzes the degradation of formaldehyde.

In a preferred embodiment, the polymer dispersant is selected from the group consisting of naphthalene formaldehyde condensates, phenol formaldehyde condensates, urea formaldehyde condensates, and melamine formaldehyde condensates.

The cross-linking agent or the polymer dispersant can be provided already mixed with the enzyme preparation or can be provided as kit, where the enzyme preparation is added to the cross-linking agent or the polymer dispersion prior to its intended uses described supra, in order to reduce the FA content of the end product. In some cases incubation time must be optimized to avoid excessive degradation of the end product.

For the purposes of the present invention, it is desirable to have the enzyme easily available in large amounts. Suitably, the enzyme is expressed in bacteria which allows for the large scale production of heterologously expressed proteins. In order to optimize the expression, i.e. increase the yield of the expressed enzyme, the inventors of the present invention have constructed a nucleic acid coding for an enzyme that catalyzes the degradation of formaldehyde.

Accordingly, another object of the present invention relates to an isolated nucleic acid coding for an enzyme that catalyzes the degradation of formaldehyde, wherein the sequence of the nucleic acid is codon-optimized for expression in an expression host.

Preferably, the expression host is *Escherichia coli.*

Although *Escherichia coli* is one example of a bacterial host cell used commonly to express an enzyme that catalyzes the degradation of formaldehyde, other bacterial host cells can be used in the present invention to express foreign DNA, including for example, *Escherichia, Enterobacter, Azotobacter, Erwinia, Bacillus, Pseudomonas, Bordetella, Rhodobacter, Xyella, Klebsielia, Proteus, Salmonella, Serratia, Shigella, Rhizobium, Vitreoscilla*, and *Paracoccus*, as well as fungal host cells, including for example, *Aspergillus, Pichia, Trichoderma, Hansenula, Saccharomyces, Kluyveromyces, Schizosaccharomyces, Chrysosporium, Candida* and *Torulopsis.*

The characteristics and advantages of codon-optimization for expression in *E. coli* are well-described in Burgess-Brown et al., Protein Expr Purif., 2008 May; 59(1):94-102.

In a preferred embodiment, the sequence of the nucleic acid comprises the sequence of SEQ ID NO:3 or a variant thereof.

Another object of the present invention refers to an expression vector containing the nucleic acid of the present invention.

Suitable vectors encompass phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotides of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride co-precipitation, DEAE-dextran-mediated transfection, lipofection, natural competence, carbon-based clusters, chemically mediated transfer, electroporation or particle bombardment (e.g., "gene-gun").

In a preferred embodiment, the vector suitable for the present invention is a nucleic acid comprising the sequence of SEQ ID NO:4, 5, and or 6.

Another aspect of the present invention refers to the use of an enzyme preparation which catalyzes the degradation of acetdehyde (AA) for reducing the acetdehyde content in an acetaldehyde-containing formulation.

As described in the definition section, AA is present in a variety of liquids and compounds, and is harmful to man. Furthermore, acetaldyde is known to be a residual compound in polyvinylalcohol. Polyvinyl alcohols are polymers of vinyl alcohol. As the latter cannot exist in free form, all polyvinyl alcohols have so far been manufactured by polymerization of vinyl acetate which, unlike vinyl alcohol, is stable. The polyvinyl acetate produced then undergoes alcoholysis. As the technical properties of polyvinyl alcohol depend in the first place on the molar mass and residual acetyl group content, industrial manufacturing processes are designed to ensure exact adherence to these parameters.

In a particularly preferred embodiment, the enzyme preparation contains an enzyme having aldehyde dismutase activity which comprises a variant or derivative of the amino acid sequence of SEQ ID NO:2, as described in more detail hereinafter, wherein the phenylalanine at position 93 and/or the isoleucine at position 301, and/or the methionine at position 337 and/or the phenylalanine at position 127 is substituted by any other amino acid.

As further illustrated by the attached figures, the analysis of the crystal structure of the formaldehyde dismutase enzyme of *Pseudomonas putida* (SEQ ID NO:2) allowed the identification of individual amino acid residues or amino acid sequence portions involved in the formation of the reactivity centre of the enzyme, so that a model system or reference enzyme for suitable further enzymes with aldehyde, in particular formaldehyde or acetaldehyde dismutase activity could be established.

In particular, for said specific reference enzyme certain key amino acid residues could be identified, which are predicted to be involved in the formation of functionally distinct portions of the substrate pocket. Said functionally distinct portions are designated catalytic site 1 (CS1), catalytic site 2 (CS2), catalytic site 3 (CS3), catalytic site 4 (CS4).

A first functional portion is CS1 and the key amino acid residue is Ile 301.

Moreover, it was found that sequence portions not adjacent to each other in the primary amino acid sequence, are nevertheless functionally related, by contributing to the same functional portion of the binding pocket. Thus, it was observed that the functional portion CS2 comprises key amino acid residue Met337.

It was also observed that said reference enzyme forms the binding pocket regions CS3 and CS4, the amino acid residues associated therewith may be further subdivided in accordance with their preferential orientation with respect to the substrate attached to the enzyme. CS3 and CS4 comprise key amino acid residues Phe127 and Phe93.

The inventors of the present invention have surprisingly found that by substituting one or more of the key amino acid residues the activity of the enzyme could be increased by at least 5%, preferably by at least 7%, more preferably by at least 10%, most preferably by 10 to 20% as compared to the activity of the wild type *Pseudomonas putida* enzyme with SEQ ID NO: 2. In addition, by substituting one or more of the key amino acid residues the thermostability of the enzyme could be increased, resulting in a stability at a temperature which is at least 1, 2, 3, 4, 5 degree Celsius higher than the temperature at which the wild type *Pseudomonas putida* enzyme with SEQ ID NO: 2 is stable. This renders the enzyme of the present invention particularly advantageous with respect to purification and expression conditions Accordingly, another object of the present invention refers to an isolated polypeptide having aldehyde dismutase activity and comprising a variant of SEQ ID NO:2 wherein the phenylalanine at position 93 of SEQ ID NO:2, and/or the isoleucine at position 301 of SEQ ID NO:2, and/or the methionine at position 337 of SEQ ID NO:2, and/or the phenylalanine at position 127 of SEQ ID NO:2 is substituted by any other amino acid.

It will be understood by the person skilled in the art that amino acids located in a close proximity to the positions of amino acids mentioned above may also be substituted. Thus, another embodiment refers to an isolated polypeptide having aldehyde dismutase activity and comprising a variant of SEQ ID NO:2, wherein an amino acid ±3, ±2 or ±1 amino acid positions from the phenylalanine at position 93 of SEQ ID NO:2, and/or an amino acid ±3, ±2 or ±1 amino acid positions from the isoleucine at position 301 of SEQ ID NO:2, and/or an amino acid ±3, ±2 or ±1 amino acid positions from the methionine at position 337 of SEQ ID NO:2, and/or an amino acid ±3, ±2 or ±1 amino acid positions from the phenylalanine at position 127 of SEQ ID NO:2 is substituted by any other amino acid.

Based on this analysis a highly characteristic sequence pattern could be developed, by means of which further candidates of proteins with the desired enzymatic activity may be searched.

Searching for further candidate enzymes by applying said sequence pattern would also be encompassed by the present invention. It will be understood by a skilled reader that the above sequence pattern is not limited by the exact distances between two adjacent amino acid residues of said pattern. Each of the distances between two neighbours in the above patterns may, for example, vary independently of each other by up to ±10, ±5, ±3, ±2 or ±1 amino acid positions without substantially affecting the desired enzymatic activity.

In line with said above functional and spatial analysis of individual amino acid residues based on the crystallographic data as obtained according to the present invention, unique partial amino acid sequences characteristic of potentially useful enzymes with aldehyde dismutase activity of the invention may be identified.

According to a further preferred embodiment the dismutation reaction is performed with isolated or purified, optionally immobilized aldehyde dismutase, or by culturing a microorganism expressing aldehyde dismutase enzyme activity as described in more detail supra.

Examples of mutants potentially having only a minor influence on the enzymatic activity are those which low or no influence on the geometry or mobility of the substrate pocket of the above-mentioned structural elements (CS1, 2, 3, or 4).

Examples of mutants potentially having a more pronounced influence on the enzymatic activity could be those which a stronger influence on the geometry or mobility of the substrate pocket or the above-mentioned structural elements (CS1, 2, 3, or 4).

With respect to the *Pseudomonas putida* protein of SEQ ID NO: 2 non-limiting examples of key amino acid substitution which may contribute to at least one of said types of mutation are listed below.

| Structural portion | Key amino acid | Mutation |
|---|---|---|
| CS1 | Ile301 | Leu, Ala, Val, Gly, Ser |
| CS2 | Met 337 | Ala |
| CS3 | Phe127 | Val, Ala |
| CS4 | Phe93 | Leu, Ile, Gly, Ala, Val |

It is to be understood by the skilled artisan that any amino acid besides the ones mentioned in the above table could be used as a substitute. Assays to test for the functionality of such mutants are readily available in the art, and respectively, described in the Example section of the present invention.

The present invention also relates to a nucleic acid as further defined hereinafter encoding a protein having aldehyde dismutase activity as defined above.

The present invention also relates to an expression cassette, comprising a nucleic acid as defined above, operably linked with at least one regulatory nucleic acid sequence.

The present invention also relates to a recombinant expression vector comprising at least one expression cassette or nucleic acid as defined above.

The present invention also relates to a recombinant microorganism, carrying at least one expression vector as defined above.

The present invention also relates to a bioreactor comprising at least one protein having aldehyde dismutase activity as defined above or a recombinant microorganism as defined above, optionally in immobilized form.

The present invention also relates to a method of preparing an enzyme with aldehyde dismutase activity, which method comprises cultivating a recombinant microorganism as defined above and optionally isolating the said aldehyde dismutase from the culture.

The present invention also relates to a crystalline form of a protein having aldehyde dismutase activity, in particular those forms, wherein the protein having aldehyde dismutase activity is as defined above.

The present invention also relates to a method of preparing a crystalline form of a protein having aldehyde dismutase activity as defined above, which method comprises adding to a solution containing said protein (in a concentration of about 1 to 50 or 5 to 20 mg/ml) and a crystallization agent (3 M to 3.5 M ammonium sulfate, preferably 3.2 M ammonium sulfate or a polyalkylene glycol, like polyethylene glycol, in particular PEG 400 to 3500, like PEG 400) having a pH in the range of 8.3 to 8.7, as for example 8.5, preferably buffered with Tris buffer.

Other Embodiments of the Invention

Proteins According to the Invention

The present invention is not limited to the specifically disclosed "proteins with aldehyde dismutase activity", but also extends to functional equivalents thereof.

"Functional equivalents" or analogs of the concretely disclosed enzymes are, within the scope of the present invention, various polypeptides thereof, which moreover possess the desired biological function or activity, e.g. enzyme activity.

For example, "functional equivalents" means enzymes, which, in a test used for enzymatic activity, display at least a 1 to 10%, or at least 20%, or at least 50%, or at least 75%, or at least 90% higher or lower activity of an enzyme, as defined herein.

"Functional equivalents", according to the invention, also means in particular mutants, which, in at least one sequence position of the amino acid sequences stated above, have an amino acid that is different from that concretely stated, but nevertheless possess one of the aforementioned biological activities. "Functional equivalents" thus comprise the mutants obtainable by one or more amino acid additions, substitutions, deletions and/or inversions, where the stated changes can occur in any sequence position, provided they lead to a mutant with the profile of properties according to the invention. Functional equivalence is in particular also provided if the reactivity patterns coincide qualitatively between the mutant and the unchanged polypeptide, i.e. if for example the same substrates are converted at a different rate. Examples of suitable amino acid substitutions are shown in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxy groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent enzymes can be determined on the basis of the concrete parameters of the invention.

"Functional equivalents" also comprise fragments, preferably individual domains or sequence motifs, of the polypeptides according to the invention, which for example display the desired biological function.

"Functional equivalents" are, moreover, fusion proteins, which have one of the polypeptide sequences stated above or functional equivalents derived there from and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" that are also included according to the invention are homologues of the concretely disclosed proteins. These possess percent identity values as stated above. Said values refer to the identity with the concretely disclosed amino acid sequences, and may be calculated according to the algorithm of Pearson and Lipman, Proc. Natl. Acad, Sci. (USA) 85(8), 1988, 2444-2448. The % identity values may also be calculated from BLAST alignments, algorithm blastp (protein-protein BLAST) or by applying the Clustal setting as given below.

A percentage identity of a homologous polypeptide according to the invention means in particular the percentage identity of the amino acid residues relative to the total length of one of the amino acid sequences concretely described herein.

In the case of a possible protein glycosylation, "functional equivalents" according to the invention comprise proteins of the type designated above in deglycosylated or glycosylated form as well as modified forms that can be obtained by altering the glycosylation pattern.

Such functional equivalents or homologues of the proteins or polypeptides according to the invention can be produced by mutagenesis, e.g. by point mutation, lengthening or shortening of the protein.

Such functional equivalents or homologues of the proteins according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

In the prior art, several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues (Arkin and Yourvan (1992) PNAS 89:7811-7815; Delgrave et al. (1993) Protein Engineering 6(3):327-331).

According to a further embodiment of the present invention, there is provided an isolated polypeptide selected from:

(i) an amino acid sequence represented by any one of SEQ ID NO: 8, or 10;

(ii) an amino acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the amino acid sequence represented by any one of SEQ ID NO: 8, or 10.

(iii) derivatives of any of the amino acid sequences given in (i) or (ii) above.

Coding Nucleic Acid Sequences

The invention also relates to nucleic acid sequences that code for enzymes as defined herein.

The present invention also relates to nucleic acids with a certain degree of "identity" to the sequences specifically disclosed herein. "Identity" between two nucleic acids means identity of the nucleotides, in each case over the entire length of the nucleic acid.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple Alignment Parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chenna, Ramu, Sugawara, Hideaki, Koike,Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, and the following Settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The invention also relates to nucleic acid sequences (single-stranded and double-stranded DNA and RNA sequences, e.g. cDNA and mRNA), coding for one of the above polypeptides and their functional equivalents, which can be obtained for example using artificial nucleotide analogs.

The invention relates both to isolated nucleic acid molecules, which code for polypeptides or proteins according to the invention or biologically active segments thereof, and to nucleic acid fragments, which can be used for example as hybridization probes or primers for identifying or amplifying coding nucleic acids according to the invention.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

According to a further embodiment of the present invention, there is therefore provided an isolated nucleic acid molecule selected from:

(i) a nucleic acid represented by any one of SEQ ID NO: 7, or 9;

(ii) the complement of a nucleic acid represented by any one of SEQ ID NO: 7, or 9;

(iii) a nucleic acid encoding the polypeptide as represented by any one of SEQ ID NO: 8, or 10, preferably as a result of the degeneracy of the genetic code, said isolated nucleic acid can be derived from a polypeptide sequence as represented by any one of SEQ ID NO: 8, or 10;

(iv) a nucleic acid having at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with any of the nucleic acid sequences of SEQ ID NO: 7, or 9;

(v) a nucleic acid molecule which hybridizes with a nucleic acid molecule of (i) to (iv) under stringent hybridization conditions;

(vi) a nucleic acid encoding a polypeptide having aldehyde dismustase activity, the polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the amino acid sequence represented by any one of SEQ ID NO: 8, or 10.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (see below) on at least about 12, preferably at least about 25, for example about 40, 50 or 75 successive nucleotides of a sense strand of a nucleic acid sequence according to the invention or of a corresponding antisense strand.

An "isolated" nucleic acid molecule is separated from other nucleic acid molecules that are present in the natural source of the nucleic acid and can moreover be substantially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences according to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These standard conditions vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of form amide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

"Hybridization" can in particular be carried out under stringent conditions. Such hybridization conditions are for example described in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions mean in particular: Incubation at 42° C. overnight in a solution consisting of 50% formamide, 5×SSC (750 mM NaCl, 75 mM tri-sodium citrate), 50 mM sodium phosphate (pH 7.6), 5×Denhardt Solution, 10% dextran sulfate and 20 g/ml denatured, sheared salmon sperm DNA, followed by washing of the filters with 0.1×SSC at 65° C.

The invention also relates to derivatives of the concretely disclosed or derivable nucleic acid sequences.

Thus, further nucleic acid sequences according to the invention can be derived from the sequences specifically disclosed herein and can differ from it by addition, substitution, insertion or deletion of individual or several nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism, as well as naturally occurring variants, e.g. splicing variants or allelic variants, thereof.

It also relates to sequences that can be obtained by conservative nucleotide substitutions (i.e. the amino acid in question is replaced by an amino acid of the same charge, size, polarity and/or solubility).

The invention also relates to the molecules derived from the concretely disclosed nucleic acids by sequence polymorphisms. These genetic polymorphisms can exist between individuals within a population owing to natural variation. These natural variations usually produce a variance of 1 to 5% in the nucleotide sequence of a gene.

Derivatives of nucleic acid sequences according to the invention mean for example allelic variants, having at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

Furthermore, derivatives are also to be understood to be homologues of the nucleic acid sequences according to the invention, for example animal, plant, fungal or bacterial homologues, shortened sequences, single-stranded DNA or RNA of the coding and non-coding DNA sequence. For example, homologues have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

Constructs According to the Invention

The invention also relates to expression constructs, containing, under the genetic control of regulatory nucleic acid sequences, a nucleic acid sequence coding for a polypeptide or fusion protein according to the invention; as well as vectors comprising at least one of these expression constructs.

"Expression unit" means, according to the invention, a nucleic acid with expression activity, which comprises a promoter as defined herein and, after functional association with a nucleic acid that is to be expressed or a gene, regulates the expression, i.e. the transcription and the translation of this nucleic acid or of this gene. In this context, therefore, it is also called a "regulatory nucleic acid sequence". In addition to the promoter, other regulatory elements may be present, e.g. enhancers.

"Expression cassette" or "expression construct" means, according to the invention, an expression unit, which is functionally associated with the nucleic acid that is to be expressed or the gene that is to be expressed. In contrast to an expression unit, an expression cassette thus comprises not only nucleic acid sequences which regulate transcription and translation, but also the nucleic acid sequences which should be expressed as protein as a result of the transcription and translation.

The terms "expression" or "overexpression" describe, in the context of the invention, the production or increase of intracellular activity of one or more enzymes in a microorganism, which are encoded by the corresponding DNA. For this, it is possible for example to insert a gene in an organism, replace an existing gene by another gene, increase the number of copies of the gene or genes, use a strong promoter or use a gene that codes for a corresponding enzyme with a high activity, and optionally these measures can be combined. Preferably such constructs according to the invention comprise a promoter 5'-upstream from the respective coding sequence, and a terminator sequence 3'-downstream, and optionally further usual regulatory elements, in each case functionally associated with the coding sequence.

A "promoter", a "nucleic acid with promoter activity" or a "promoter sequence" mean, according to the invention, a nucleic acid which, functionally associated with a nucleic acid that is to be transcribed, regulates the transcription of this nucleic acid.

"Functional" or "operative" association means, in this context, for example the sequential arrangement of one of the nucleic acids with promoter activity and of a nucleic acid sequence that is to be transcribed and optionally further regulatory elements, for example nucleic acid sequences that enable the transcription of nucleic acids, and for example a terminator, in such a way that each of the regulatory elements can fulfill its function in the transcription of the nucleic acid sequence. This does not necessarily require a direct association in the chemical sense. Genetic control sequences, such as enhancer sequences, can also exert their function on the target sequence from more remote positions or even from other DNA molecules. Arrangements are preferred in which the nucleic acid sequence that is to be transcribed is positioned behind (i.e. at the 3' end) the promoter sequence, so that the two sequences are bound covalently to one another. The distance between the promoter sequence and the nucleic acid sequence that is to be expressed transgenically can be less than 200 bp (base pairs), or less than 100 bp or less than 50 bp.

Apart from promoters and terminators, examples of other regulatory elements that may be mentioned are targeting sequences, enhancers, polyadenylation signals, selectable markers, amplification signals, replication origins and the like. Suitable regulatory sequences are described for example in Goeddel, Gene Expression Technology: Methods in Enzymology 185, Academic Press, San Diego, Calif. (1990).

Nucleic acid constructs according to the invention comprise in particular sequences selected from those, specifically mentioned herein or derivatives and homologues thereof, as well as the nucleic acid sequences that can be derived from amino acid sequences specifically mentioned herein which are advantageously associated operatively or functionally with one or more regulating signal for controlling, e.g. increasing, gene expression.

In addition to these regulatory sequences, the natural regulation of these sequences can still be present in front of the actual structural genes and optionally can have been altered genetically, so that natural regulation is switched off and the expression of the genes has been increased. The nucleic acid construct can also be of a simpler design, i.e. without any additional regulatory signals being inserted in front of the coding sequence and without removing the natural promoter with its regulation. Instead, the natural regulatory sequence is silenced so that regulation no longer takes place and gene expression is increased.

A preferred nucleic acid construct advantageously also contains one or more of the aforementioned enhancer sequences, functionally associated with the promoter, which permit increased expression of the nucleic acid sequence. Additional advantageous sequences, such as other regulatory elements or terminators, can also be inserted at the 3' end of the DNA sequences. One or more copies of the nucleic acids according to the invention can be contained in the construct. The construct can also contain other markers, such as antibiotic resistances or auxotrophy-complementing genes, optionally for selection on the construct.

Examples of suitable regulatory sequences are contained in promoters such as cos-, tac-, trp-, tet-, trp-tet-, lpp-, lac-, lpp-lac-, $lacI^{q-}$, T7-, T5-, T3-, gal-, trc-, ara-, rhaP (rhaPBAD) SP6-, lambda-$P_R$- or in the lambda-$P_L$ promoter, which find application advantageously in Gram-negative bacteria. Other advantageous regulatory sequences are contained for example in the Gram-positive promoters ace, amy and SPO2, in the yeast or fungal promoters ADC1, MFalpha, AC, P-60, CYC1, GAPDH, TEF, rp28, ADH. Artificial promoters can also be used for regulation.

For expression, the nucleic acid construct is inserted in a host organism advantageously in a vector, for example a plasmid or a phage, which permits optimum expression of the genes in the host. In addition to plasmids and phages, vectors are also to be understood as meaning all other vectors known to a person skilled in the art, e.g. viruses, such as SV40, CMV, baculovirus and adenovirus, transposons, IS elements, phasmids, cosmids, and linear or circular DNA. These vectors can be replicated autonomously in the host organism or can be replicated chromosomally. These vectors represent a further embodiment of the invention.

Suitable plasmids are, for example in *E. coli*, pLG338, pACYC184, pBR322, pUC18, pUC19, pKC30, pRep4, pHS1, pKK223-3, pDHE19.2, pHS2, pPLc236, pMBL24, pLG200, pUR290, pIN-$III^{113}$-B1, λgt11 or pBdCl; in nocardioform actinomycetes pJAM2; in Streptomyces pIJ101, pIJ364, pIJ702 or pIJ361; in *bacillus* pUB110, pC194 or pBD214; in Corynebacterium pSA77 or pAJ667; in fungi pALS1, pIL2 or pBB116; in yeasts 2alphaM, pAG-1, YEp6, YEp13 or pEMBLYe23 or in plants pLGV23, $pGHlac^+$, pBIN19, pAK2004 or pDH51. The aforementioned plasmids represent a small selection of the possible plasmids. Other plasmids are well known to a person skilled in the art and will be found for example in the book Cloning Vectors (Eds. Pouwels P. H. et al. Elsevier, Amsterdam-New York-Oxford, 1985, ISBN 0 444 904018).

In a further embodiment of the vector, the vector containing the nucleic acid construct according to the invention or the nucleic acid according to the invention can be inserted advantageously in the form of a linear DNA in the microorganisms and integrated into the genome of the host organism through heterologous or homologous recombination. This linear DNA can comprise a linearized vector such as plasmid or just the nucleic acid construct or the nucleic acid according to the invention.

For optimum expression of heterologous genes in organisms, it is advantageous to alter the nucleic acid sequences in accordance with the specific codon usage employed in the organism. The codon usage can easily be determined on the basis of computer evaluations of other, known genes of the organism in question.

The production of an expression cassette according to the invention is based on fusion of a suitable promoter with a suitable coding nucleotide sequence and a terminator signal or polyadenylation signal. Common recombination and cloning techniques are used for this, as described for example in T. Maniatis, E. F. Fritsch and J. Sambrook, Molecular Cloning: A Laboratory Manual, Cold Spring Harbor Laboratory, Cold Spring Harbor, N.Y. (1989) as well as in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

The recombinant nucleic acid construct or gene construct is inserted advantageously in a host-specific vector for expression in a suitable host organism, to permit optimum expression of the genes in the host. Vectors are well known to a person skilled in the art and will be found for example in "Cloning Vectors" (Pouwels P. H. et al., Publ. Elsevier, Amsterdam-New York-Oxford, 1985).

Hosts that can be used according to the invention

Depending on the context, the term "microorganism" means the starting microorganism (wild-type) or a genetically modified microorganism according to the invention, or both.

The term "wild-type" means, according to the invention, the corresponding starting microorganism, and need not necessarily correspond to a naturally occurring organism.

By means of the vectors according to the invention, recombinant microorganisms can be produced, which have been transformed for example with at least one vector according to the invention and can be used for production of the polypeptides according to the invention. Advantageously, the recombinant constructs according to the invention, described above, are inserted in a suitable host system and expressed. Preferably, common cloning and transfection methods that are familiar to a person skilled in the art are used, for example co-precipitation, protoplast fusion, electroporation, retroviral transfection and the like, in order to secure expression of the stated nucleic acids in the respective expression system. Suitable systems are described for example in Current Protocols in Molecular Biology, F. Ausubel et al., Publ. Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

In principle, all prokaryotic organisms can be considered as recombinant host organisms for the nucleic acid according to the invention or the nucleic acid construct. Bacteria are used advantageously as host organisms. Although *Escherichia coli* is one example of a bacterial host cell used commonly to express an enzyme that catalyzes the degradation of formaldehyde, other bacterial host cells can be used in the present invention to express foreign DNA, including for example, *Escherichia, Enterobacter, Azotobacter, Erwinia, Bacillus, Pseudomonas, Bordetella, Rhodobacter, Xyclla, Klebsielia, Proteus, Salmonella, Serratia, Shigella, Rhizobium, Vitreoscilla*, and *Paracoccus*. Furthermore, eukaryotic fungal host cells can be used in the present invention to express foreign DNA, including for example, *Aspergillus, Pichia, Trichoderma, Hansenula, Saccharomyces, Kluvveromyces, Schizosaccharomyces, Chrysosporium, Candida* and *Torulopsis*.

The host organism or host organisms according to the invention then preferably contain at least one of the nucleic acid sequences, nucleic acid constructs or vectors described in this invention, which code for an enzyme activity according to the above definition.

The organisms used in the method according to the invention are grown or bred in a manner familiar to a person skilled in the art, depending on the host organism. As a rule, microorganisms are grown in a liquid medium, which contains a source of carbon, generally in the form of sugars, a source of nitrogen generally in the form of organic sources of nitrogen such as yeast extract or salts such as ammonium sulfate, trace elements such as iron, manganese and magnesium salts and optionally vitamins, at temperatures between 0° C. and 100° C., preferably between 10° C. to 60° C. with oxygen aeration. The pH of the liquid nutrient medium can be maintained at a fixed value, i.e. regulated or not regulated during growing. Growing can be carried out batchwise, semi-batchwise or continuously. Nutrients can be supplied at the start of fermentation or can be supplied subsequently, either semi-continuously or continuously.

Recombinant production proteins with aldehyde dismutase activity

The invention also relates to methods for production of proteins according to the invention by cultivating a microorganism which expresses said protein, and isolating the desired product from the culture.

The microorganisms as used according to the invention can be cultivated continuously or discontinuously in the batch process or in the fed batch or repeated fed batch process. A review of known methods of cultivation will be found in the textbook by Chmiel (Bioprocesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D.C., USA, 1981).

These media that can be used according to the invention generally comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soybean protein, yeast extract, meat extract and others. The sources of nitrogen can be used separately or as a mixture. Inorganic salt compounds that may be present in the media comprise the chloride, phosphate or sulfate salts of calcium, magnesium, sodium, cobalt, molybdenum, potassium, manganese, zinc, copper and iron. Inorganic sulfur-containing compounds, for example sulfates, sulfites, dithionites, tetrathionates, thiosulfates, sulfides, but also organic sulfur compounds, such as mercaptans and thiols, can be used as sources of sulfur.

Phosphoric acid, potassium dihydrogenphosphate or dipotassium hydrogenphosphate or the corresponding sodium-containing salts can be used as sources of phosphorus. Chelating agents can be added to the medium, in order to keep the metal ions in solution. Especially suitable chelating agents comprise dihydroxyphenols, such as catechol or protocatechuate, or organic acids, such as citric acid. The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (Publ. P. M. Rhodes, P. F. Stanbury, IRL Press (1997) p. 53-73, ISBN 0 19 963577 3). Growing media can also be obtained from commercial suppliers, such as Standard 1 (Merck) or BHI (Brain heart infusion, DIFCO) etc. All components of the medium are sterilized, either by heating (20 min at 1.5 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 10 hours to 160 hours.

The cells can be disrupted optionally by high-frequency ultrasound, by high pressure, e.g. in a French pressure cell, by osmolysis, by the action of detergents, lytic enzymes or organic solvents, by means of homogenizers or by a combination of several of the methods listed.

Particular use of the enzyme having aldehyde dismutase activity

The invention also relates to the use of an isolated polypeptide having aldehyde dismutase activity and comprising a variant of SEQ ID NO:2 wherein the phenylalanine at position 93 of SEQ ID NO:2, and/or the isoleucine at position 301 of SEQ ID NO:2, and/or the methionine at position 337 of SEQ ID NO:2, and/or the phenylalanine at position 127 of SEQ ID NO:2 is substituted by any other amino acid, for reducing the aldehyde content in an aldehyde-containing formulation.

In a preferred embodiment, the aldehyde is acetaldehyde as defined in the definition section.

In another preferred embodiment, the aldehyde is methylglyoxal.

The following examples only serve to illustrate the invention. The numerous possible variations that are obvious to a person skilled in the art also fall within the scope of the invention.

EXAMPLES

Example 1

FDM Expression & Purification

The following procedure is derived from a previously described protocol (Yanase, H., Moriya, K., Mukai, N., Kawata, Y., Okamoto, K., Kato, N. (2002) Effects of GroESL Coexpression on the Folding of Nicotinoprotein Formaldehyde Dismutase from *Pseudomonas putida* F61 Biosci. Bitechnol. Biochem., 66(1), 85-91) and has been further optimized. The codon usage of the gene coding for FDM has been optimized for *E. coli*. The new DNA sequence has been synthesized and cloned into pDHE, a rhamnose-inducible expression vector (SEQ ID NO:4). The GroEL/S chaperones, which are necessary for soluble FDM production, are cloned in the IPTG-inducible pAgro vector (SEQ ID NO:5). The lac repressor is encoded by the pHSG vector (SEQ ID NO:6). Expression of FDM has been performed using *E. coli* TG10, a TG1 derivative with no rhamnose isomerase. TG10 cells containing pAgro and pHSG (TG10+) were transformed with pDHE-FDM and cultured in LB for 5 h at 37° C. in presence of ampicillin (pDHE), spectinomycin (pAgro) and chloramphenicol (pHSG). 5 mL of this culture were transferred in 500 mL of the same medium containing 100 μM IPTG and 0.5 g/L rhamnose. Induction was performed at 37° C. for about 18 h. Cells were collected by centrifugation and resuspended in lysis buffer (10 mM $KH_2PO_4$, pH 7, 0.5 mM $MgCl_2$, 140 μM PMSF). Cell lysis was induced by sonication (<1', 1 s/1 s>×10, 70% amplitude). After 10' incubation at 37° C. and centrifugation, ammonium sulfate was added to the clear lysate to a saturation of 50%. Unwanted proteins (e.g. chaperones) were allowed to precipitate for 2-4 h on ice.

The precipitate was removed by centrifugation and the clear FDM-containing solution was applied to a Phenyl SEPHAROSE® column (HIC chromatography). The FDM-containing fractions were eluted using a "40% to 0%" ammonium sulfate gradient (buffer: 10 mM $KH_2PO_4$, 0.5 mM $MgCl_2$, pH 7.2). The presence of FDM was confirmed by a quick colorimetric assay: 10 μL of each fraction was transferred to a 96-well MTP plate and incubated with 250 μL of a formaldehyde solution (12.5 ppm in 100 mM $KH_2PO_4$, pH 7, 30'). Unreacted formaldehyde was detected by addition of 50 μL PURPALD® reagent (10 mg/mL in 1 M NaOH, Sigma) to 50 μL reaction mix. Color development indicates absence of enzyme in the collected fraction.

After the Phenyl SEPHAROSE ® purification step, the eluted fractions were concentrated by ultrafiltration (10 kDa cut off) and desalted by size-exclusion chromatography (HIPREP® Desalting 26/10 mL, Amersham). 10 mM $KH_2PO_4$, 0,5 mM $MgCl_2$ (pH 7) was used as running buffer. The protein solution was concentrated by ultrafiltration (10 kDa cut off) and glycerol was added to a final concentration of 50%. FDM stocks (2-5 mg/mL) were stored at -20 ° C. This procedure allows protein purification to homogeneity, as judged by Coomassie-stained SDS-PAGE (data not shown).

For FDM mutants the following method is employable as well

The following procedure is derived from a previously described protocol (Yanase et al. 2002, Biosci. Biotechnol. Biochem., 66(1), 85-91) and has been further optimized. The codon usage of the gene coding for FDM (or mutant) has been optimized for *E. coli* (SEQ ID NO:3). The new DNA sequence has been synthesized and cloned into pDHE, a rhamnose-inducible expression vector (SEQ ID NO:4). The GroEL/S chaperones, which are necessary for soluble FDM production, are cloned in the IPTG-inducible pAgro vector (SEQ ID NO:5). The lac repressor is encoded by the pHSG vector (SEQ 1N NO:6). Expression of FDM has been performed using *E. coli* TG10, a TG1 derivative with no rhamnose isomerase. TG10 cells containing pAgro and pHSG (TG10+) were transformed with pDHE-FDM and cultured in LB for 5 h at 37° C. in presence of ampicillin (pDHE), spectinomycin (pAgro) and chloramphenicol (pHSG). 5 mL of this culture were transferred in 500 mL of the same medium containing 100 μM IPTG and 0.5 g/L rhamnose. Induction was performed at 37° C. for about 18 h. Cells were collected by centrifugation and resuspended in lysis buffer (10 mM $KH_2PO_4$, pH 7, 0.5 mM $MgCl_2$). Cell lysis was induced by sonication (<3', 15 s/15 s>×3, 85% amplitude). After 10' incubation at 37° C. and centrifugation, ammonium sulfate was added to the clear lysate to a saturation of 50%. Unwanted proteins (e.g. chaperones) were allowed to precipitate for 1-2 h on ice.

The precipitate was removed by centrifugation and the clear FDM-containing solution was applied to a Phenyl SEPHAROSE® column (HIC chromatography). The FDM-containing fractions were eluted using a "40% to 0%" ammonium sulfate gradient (buffer: 10 mM $KH_2PO_4$, 0.5 mM $MgC1_2$, pH 7.2). The presence of FDM was confirmed by a quick colorimetric assay: 10 μL of each fraction was transferred to a 96-well MTP plate and incubated with 250 μL of a formaldehyde solution (12.5 ppm in 100 mM $KH_2PO_4$, pH 7, 30'). Unreacted formaldehyde was detected by addition of 50 μL PURPALD® reagent (10 mg/mL in 1 M NaOH, Sigma) to 50 μL reaction mix. Color development indicates absence of enzyme in the collected fraction.

After the Phenyl SEPHAROSE ® purification step, the eluted fractions were concentrated by ultrafiltration (10 kDa cut off) and desalted by size-exclusion chromatography (HIPREP® Desalting 26/10 mL, Amersham). 10 mM $KH_2PO_4$, 0,5 mM $MgCl_2$ (pH 7) was used as running buffer. The protein solution was concentrated by ultrafiltration (10 kDa cut off) and glycerol was added to a final concentration of 50%. FDM stocks (2-5 mg/mL) were stored at -20 ° C. This procedure allows protein purification to homogeneity, as judged by Coomassie-stained SDS-PAGE (data not shown).

Example 2

FDM Characterization by pH-Stat Titration

FDM activity was assayed in a standard reaction mixture containing 20 mM formaldehyde, 100 mM KCl, 0.25 mM $KH_2PO_4$ (pH 7). The reaction was performed at RT by adding 5 μL of enzyme solution to 25 mL of standard mixture. Formate formation was monitored over 5' by pH-stat titration with 5 mM NaOH. One unit is defined as the amount of enzyme necessary to catalyze the formation of 1 μmol formic acid per minute. FDM expressed in TG10+ had a specific activity ranging between 100-200 U/mg.

Example 3

Detection of Formaldehyde

The detection principle of the LAW 112 method relies on the reaction of formaldehyde with acetylacetone in the presence of ammonia to form the yellow compound 3,5-diacetyl-1,4-dihydrolutidine (Hantzsch reaction) (Nash, T. (1953) The Colorimetric Estimation of Formaldehyde by Means of the Hantzsch Reaction Biochem. J., 55(3), 416-421 and Fregert, S., Dahlquist, I., Gruvberger, B. (1984) A Simple Method for the Detection of Formaldehyde Contact Dermatitis, 10, 132-134). For a quantitative formaldehyde detection, a reagent solution is prepared as follows: 15 g ammonium acetate, 0.2 mL acethylacetone, 0.3 mL acetic acid are mixed in 100 mL distilled water (stable for 1 week at 4° C.). Aqueous solutions of formaldehyde ranging from 5 ppm to 25 ppm are prepared for the calibration curve. The reaction is started by mixing 0.1 mL of an aqueous sample solution (or standard or water as blank) with 0.15 mL of reagent solution and incubated at 60° C. for 10'. After the solution has cooled down to RT, distilled water is added to a final volume of 1 mL. Formation of 3,5-diacetyl-1,4-dihydrolutidine is monitored at 412 nm.

Example 4

Preliminary Enzyme Characterization

In order to determine the efficiency of formaldehyde dismutase for textile applications, different enzyme concentrations were incubated with 220 ppm formaldehyde in 100 mM $KH_2PO_4$, pH 8, RT, 30'. The samples were analyzed by the previously described acetylacetone method. Specific activity of the enzyme stock solution was 165 U/mg. The results are shown in table 1.

TABLE 1

Enzymatic formaldehyde removal in solution (220 ppm formaldehyde). Detection by the acethylacetone method. Values indicate remaining formaldehyde in solution after 30' incubation at RT.

| FDM (mg/L) | Formaldehyde (ppm) |
|---|---|
| 0 | 230 |
| 7 | 11 |
| 17 | not detectable (<<5 ppm) |

Even very low enzyme concentrations are more than sufficient to reduce the formaldehyde content almost completely. Another interesting property for technical applications is the tolerance to alcohols (ethanol, isopropanol) or pure water instead of buffer. To that end, 17 mg/L formaldehyde dismutase were incubated at 30° C. in 100 mM $KH_2PO_4$ (pH 8), 220 ppm formaldehyde and 10 or 20% v/v solvent (ethanol or isopropanol). Alternatively, $ddH_2O$ was used instead of phosphate buffer. The results are summarized in table 2.

TABLE 2

Effect of ethanol, isopropanol (in % v/v) and pure water on FDM activity (FDM at 17 mg/L, formaldehyde 220 ppm). Values indicate remaining formaldehyde in solution after 30' incubation at 30° C. Detection by the acethylacetone method.

| FDM in 10% EtOH | FDM in 20% EtOH | 20% EtOH |
|---|---|---|
| 160 ppm | 196 ppm | 227 ppm |
| FDM in 10% isopropanol | FDM in 20% isopropanol | 20% isopropanol |
| 26 ppm | 104 ppm | 229 ppm |
| FDM in $ddH_2O$ | $ddH_2O$ | |
| 240 ppm (133 ppm after 90') | 201 ppm (202 ppm after 90') | |

Formaldehyde dismutase from *P. putida* F61 does not effectively react with FA in the presence of large amounts of ethanol. Even at 10% v/v, enzyme activity towards FA is strongly inhibited. Relatively low concentrations of isopropanol are not problematic, but more than 10% v/v have a negative effect on activity. Pure water inactivates the enzyme; generation of formic acid induces an acidic pH-shift (pH drops from 7 to about 4).

Example 5

Treatment of Finished Textiles with FDM

Figure 3:
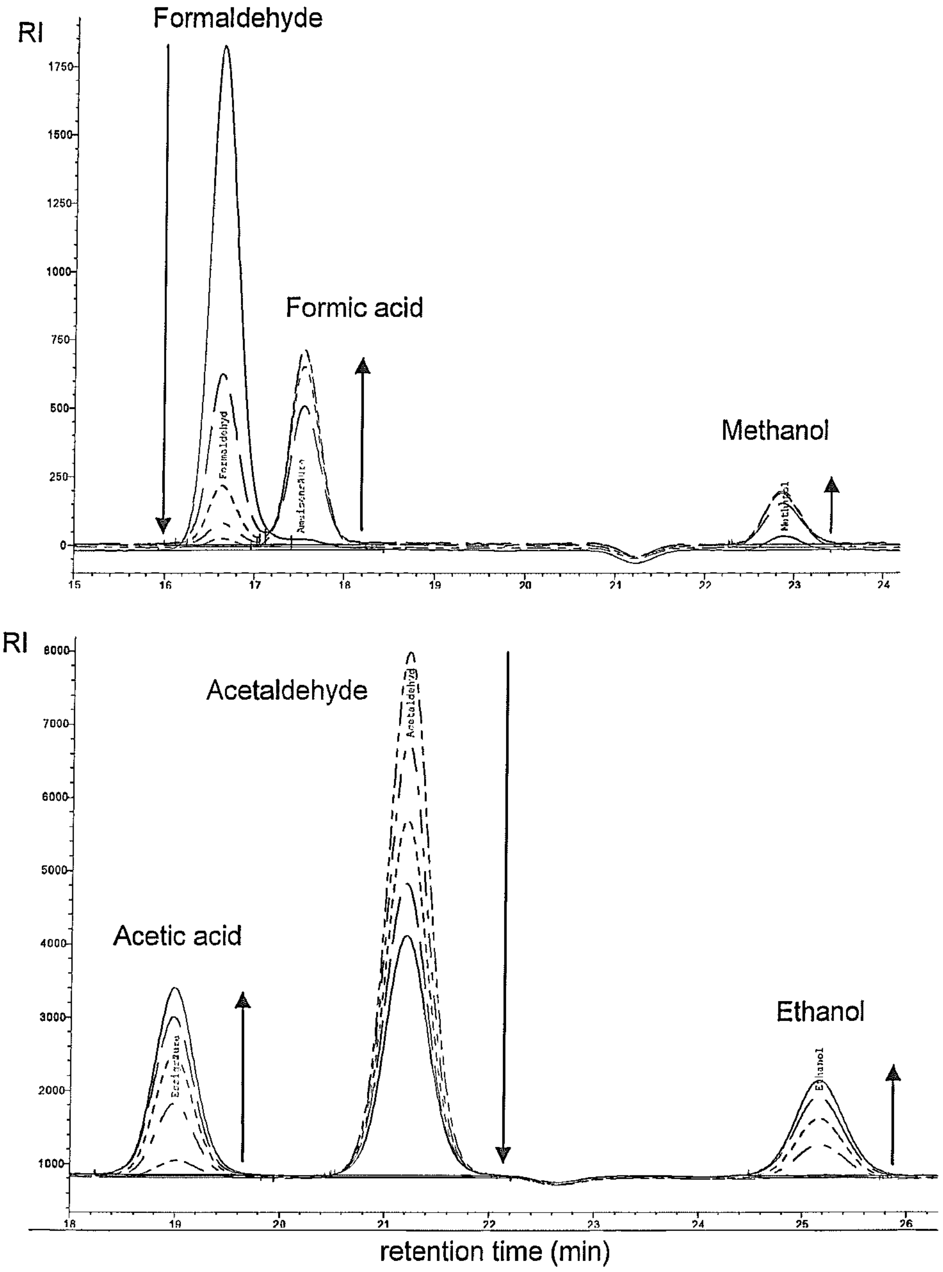
FIG. 3: Enzymatic conversion of formaldehyde (top) and acetaldehyde (bottom) followed over time by HPLC using the FDM $I^{301}L$ variant. The reaction mixture was analyzed in 30' intervals over 2 h. The reactions were performed in 50 mM $K_2HPO_4$ (pH 7.3 for formaldehyde and pH 8 for acetaldehyde), 100 mM KCl and 20 mM aldehyde. Enzyme concentration for acetaldehyde was 50 μg/mL and for formaldehyde 2.4 μg/mL. Retention time formaldehyde: 16.6 min; formic acid: 17.5 min; methanol: 22.9 min; acetaldehyde: 21.2 min; acetic acid: 18.9 min; ethanol: 25.2 min. Product generation is equimolar. Detection by RI.

Cotton fiber finished with a dimethyloldihydroxyethylene urea cross-linker has been treated with FDM. After condensation of the cross-linker with the cotton fiber, about 114 ppm of free formaldehyde in the textile could be determined by the acethylacetone method. This textile sample has been subsequently impregnated with enzyme solutions of different concentrations (100 mM $KH_2PO_4$, pH 8, 0-150 mg/L enzyme) and immediately passed through two rotating metal cylinders (FIG. 3). The wet sample was incubated for 60' at 30° C. Formaldehyde extracted from 1 g of textile sample was quantified by the acetylacetone method (LAW 112). Table 3 summarizes the data.

TABLE 3

Effect of different FDM concentrations on cotton cross-linked with a modified dimethy-loldihydroxyethylene urea cross-linker (114 ppm formaldehyde in the textile before the enzymatic treatment).

| FDM (mg/L) | formaldehyde from wet textile (ppm) | Formaldehyde from dry textile (ppm) |
|---|---|---|
| 0 | 73 | 95 |
| 20 | 33 | 56 |
| 50 | 22 | 40 |
| 100 | 23 | 51 |
| 150 | 23 | 49 |

The formaldehyde content with no dismutase has decreased to about 70 ppm (95 from dry textile) probably due to some "wash-out"-effect during the impregnation process. In general, formaldehyde dismutase is able to clearly lower the amount of extracted formaldehyde to levels between 20 and 40 ppm. Differences in the wet vs. dry formaldehyde detection are probably due to differences in the textile water-content estimations. Table 4 shows the same experiment performed on textile cross-linked with an alternative dimethyloldihydroxyethylene urea crosslinker containing a larger amount of FA (641 ppm formaldehyde in the textile before the enzymatic treatment).

TABLE 4

Effect of different FDM concentrations on cotton cross-linked with a dimethyloldihydroxyethylene urea formulation.

| | 30' incubation | | 60' incubation | |
|---|---|---|---|---|
| FDM (mg/L) | formaldehyde from wet textile (ppm) | formaldehyde from dry textile (ppm) | Formaldehyde from wet textile (ppm) | Formaldehyde from dry textile (ppm) |
| 0 | 342 | 345 | 363 | 355 |
| 20 | 150 | 188 | 127 | 190 |
| 50 | 100 | 156 | 69 | 126 |
| 100 | 86 | 159 | 59 | 123 |
| 150 | 80 | 146 | 59 | 116 |

Due to a "wash-out" effect, the samples with no dismutase show a clear drop in the formaldehyde content. Nevertheless, application of increasing amounts of dismutase leads to a clear reduction of released formaldehyde from the finished textile. A water uptake of about 70% means that about 100 mg dismutase per kg textile are more than sufficient to substantially reduce the formaldehyde content.

In order to reduce time and energy costs to dry the textile after the enzymatic treatment, it would be beneficial to reduce the water content in such applications. To that end, crosslinked textile samples have been treated slightly differently: a concentrated enzyme solution (1350 mg/L in 1×PBS, 25% glycerol) was sprayed on the textile. The water uptake was fine-tuned, allowing the range 0-50% humidity to be analyzed (Table 5). All textile probes were incubated for 60' at 30° C.

TABLE 5

Effect of different water uptake on cotton cross-linked with a dimethyloldihydroxyethylene urea formulation (641 ppm formaldehyde in the textile before the enzymatic treatment). FDM was sprayed as a concentrated stock solution (1350 mg/L in 1x PBS, 25% glycerol).

| samples | water uptake of the textile sample (w/w %) | Formaldehyde from dry textile (ppm) |
|---|---|---|
| buffer only | 20 | 465 |
| +FDM | 10 | 346 |
| +FDM | 20 | 222 |
| +FDM | 30 | 180 |
| +FDM | 40 | 167 |
| +FDM | 50 | 160 |

Even by applying the enzyme as a spray, some "wash-out" of formaldehyde was unavoidable (20% buffer uptake, 465 ppm released formaldehyde). Nevertheless, the enzyme application with the same water uptake (270 mg enzyme per kg textile) still resulted in more than 50% reduction in released formaldehyde. Compared to the enzyme application through the metal cylinders, where the water content of the textile reaches 70%, the efficiency of the spray application is less pronounced.

Example 6

Effect of FDM on the FA-Content of Different Textile Finishing Products

An alternative strategy to reduce the formaldehyde amount in textiles would be to apply the dismutase directly on the cross-linker solution, before the condensation step with the textile. To that end, 3 products have been tested with formaldehyde dismutase: a dimethyloldihydroxyethylene urea formulation (formulation 1), a methoxymethylated melamine formulation (formulation 2) and a polycondensated methoxymethylated melamine formulation with low FA content (formulation 3). The cross-linker formulation 1 is a highly concentrated, slightly acidic (pH 5-6) aqueous solution which contains between 0.1 and 1% formaldehyde (1000 to 10.000 ppm). Formulation 2, is a concentrated aqueous solution (pH 8-9) containing between 1.5 and 2.5% formaldehyde. Formulation 3 is a slightly basic aqueous solution containing between 0.2 and 1% formaldehyde (pH 8-9).

Typically, 87 μL of pure product were mixed with 10 μL of 3 M $KH_2PO_4$ (pH 7) and 3 μL of 50% glycerol (negative control). In the enzyme-treated samples, a enzyme stock solution (4.8 mg/mL) was used instead of glycerol. The final enzyme concentration in the product solution was ~150 mg/L. Formaldehyde was detected by the acetylacetone method. Table 6 shows the effect of FDM on cross-linker solutions.

TABLE 6

Effect of FDM (~150 mg/L) on Formulation 1, 2 and 3. The reaction-mix was buffered with ca. 300 mM $KH_2PO_4$ (pH 7) and incubated for 60' at 30° C. Values indicate remaining formaldehyde after treatment (in ppm) in the concentrated product. Detection by the acetylacetone method.

| cross-linker | −FDM | +FDM |
|---|---|---|
| formulation 1 | 5200 | 1700 |
| formulation 3 | 3500 | 1700 |
| formulation 2 | 38.000 | 29.300 |

The best results were obtained on formulation 1 with approximately 70% reduction in the formaldehyde content. The formaldehyde content of formulation 3 was reduced by about 50%. Treatment of formulation 2 with FDM only reduced the high formaldehyde content by 20%. Note that a prolonged exposure to FDM can lead to product degradation.

Overall, these preliminary results indicate that FDM could potentially be applied directly on the product solutions.

Example 7

Use of FDM to Reduce the FA-Content in Modified Dimethyloldihydroxyethylene Urea Compounds Crosslinking agents are used for easy-care finishing of textiles made of cellulosic fibres and their blends with synthetic fibers. An important class of these chemicals is the class of modified dimethyloldihydroxyethylene urea compounds. Here we treated 4 different product formulations with formaldehyde dismutase (FDM) and measured the remaining formaldehyde in the product. Moreover, enzyme-treated product was used in cotton-finishing. Formaldehyde-content of the textile (cotton) and the performance of finishing have been quantified.

Product formulations were treated as follows: 17.4 g of crosslinking reagent (as concentrated aqueous solution) and 2 mL of 3M $KH_2PO_4$ (pH 7) were gently mixed with 0.6 mL of FDM (4.8 mg/mL). The final enzyme concentration was about 140 mg/L. The enzymatic process was carried out at RT for about 3 h. The formaldehyde content was measured as previously described (acetylacetone method) (see Table 7).

TABLE 7

| crosslinking reagent | FA (ppm) with FDM | FA (ppm) no FDM |
|---|---|---|
| 1 | 1200 | 4100 |
| 2 | 500 | 3100 |
| 3 | 500 | 2200 |
| 4 | 500 | 3500 |

The formaldehyde content in the product solutions was reduced by 70-80%. Formaldehyde removal in product 1 (unprotected methylol groups) can lead to product degradation over time.

The enzyme-treated and non-treated formulations were used in cotton finishing (textile: CO-Popelin, using the following recipe: 57.5 g/L crosslinking reagent, 10 g/L $MgCl_2.6H_2O$, pH 5.0 (by adding acetic acid). The cotton samples (pick-up about 70%) were allowed to dry at 110° C. to a final humidity of about 6%. The following curing step was performed at 150° C. for 3 minutes. The formaldehyde content in the cotton sample was measured by LAW 112 (values in ppm). Additional performance indicators were dry crease recovery angles (dcra) (in °), tensile strength (tensile in N on 40*100 mm), smoothness rating Durable Press (DP rating), smoothness rating Monsanto (Monsanto rating), shrinkage (warp (w) & weft (f) in %). The following table (Table 8) summarizes the results (1: non-finished cotton 2: formulation 1 3: formulation 1+FDM 4: formulation 2 5: formulation 2+FDM 6: formulation 3 7: formulation 3+FDM 8: formulation 4 9: formulation 4+FDM).

TABLE 8

| | 1 | 2 | 3 | 4 | 5 | 6 | 7 | 8 | 9 |
|---|---|---|---|---|---|---|---|---|---|
| FA (LAW 112) | 1 | 196 | 168 | 53 | 25 | 35 | 22 | 42 | 22 |
| dcra | 123 | 198 | 187 | 187 | 178 | 180 | 187 | 180 | 173 |
| tensile | 399 | 361 | 356 | 340 | 282 | 304 | 350 | 342 | 324 |
| DP rating | 1 | 2 | 2 | 1.5 | 1.5 | 1.5 | 1.5 | 1.5 | 1.5 |
| Monsanto rating | 1 | 3 | 3 | 2 | 2 | 2.5 | 2.5 | 2.5 | 2.5 |
| Shrinkage w | 4.0 | 1.4 | 1.4 | 2.0 | 1.6 | 1.8 | 2 | 2 | 1.8 |
| Shrinkage f | 0.2 | 0.4 | 0.4 | 0.0 | 0.2 | 0.2 | 0 | 0.2 | 0.2 |

Example 8

Use of FDM to Reduce the FA-Content in Sulphonated Melamine-FA Polycondensates Used as Polymeric Dispersants/Superplasticizers Sulfonated melamine-FA polycondensates are especially optimized for plastification and water reduction of cement and calcium sulphate based mixtures. Typically, these products are used as a 20% w/v aqueous solution and the pH-value is about 9 to 11.4 (sample 1) and 7 to 10 (sample 2). Here (see Table 9) we treated the 20% w/v working-solutions of both samples with FDM (final concentration 140 mg/L) and quantified the remaining formaldehyde after different incubation-time using the previously described acetylacetone method (values in ppm).

TABLE 9

| 20% w/v | No FDM | FDM (1 h) | FDM (3 h) | FDM (24 h) |
|---|---|---|---|---|
| sample 1 | 5700 | 3200 | 2500 | 1800 |
| sample 2 | 1700 | 1200 | 1000 | 700 |

Product performance after 1 h enzymatic treatment was not negatively affected with respect to set time, flow and strength. Similar results can be obtained by using as much as ⅕ of the enzyme concentration. In these products, removal of formaldehyde can lead to changes in the molecular weight distribution of the polymer over time.

Example 9

Use of FDM to Reduce the FA-Content in a Modified Anionic Polyalkylglycol-Phenol-FA Resin Modified anionic polyalkyl-phenol-aldehyde resins are especially optimized for plastification and water reduction of cement and calcium sulphate based mixtures. The product is formulated as a concentrated aqueous solution (pH 5-8). Enzyme treatment was performed by adding FDM directly to the product. Non-treated product contains about 250 ppm formaldehyde, as determined by the acethylacetone method. The following table (Table 10) shows the remaining formaldehyde (in ppm) after 0.5 h, 3 h and 24 h incubation with FDM.

TABLE 10

| | FDM (30 min) | FDM (3 h) | FDM (24 h) |
|---|---|---|---|
| FDM (100 mg/L) | 10.2 | 6.8 | 3.5 |
| FDM (10 mg/L) | 125.5 | 26.1 | 2.4 |

Product performance after 1 h of enzymatic treatment was not negatively affected with respect to set time, flow and strength.

Similar results can be obtained using non-purified cell extracts or whole cells producing FDM.

Example 10

Rational Design of FDM for Expanded Substrate Specificity

The active site of FDM shows the formaldehyde molecule bound in a relatively narrow, predominantly hydrophobic pocket. A strategically positioned zinc ion is acting as a Lewis acid and activates the substrate for a nucleophilic attack by a hydrid ion donated by a tightly bound NADH cofactor molecule. The postulated reaction mechanism of the dismutation reaction consists of two coupled half-reactions. In the first half-reaction one formaldehyde molecule is oxidized irreversibly by the enzyme (E)-$NAD^+$ complex to form formic acid and the (E)-NADH complex. In the second half-reaction another formaldehyde molecule binds to the (E)-NADH complex and is irreversibly reduced to methanol, leaving behind the (E)-$NAD^+$ complex for the next reaction. The postulated reaction mechanism for the dismutation catalyzed by FDM is described and illustrated in Tanaka et al. (2002), Journal of Molecular Biology, 324, 519-533. The active site of FDM from *P. putida* F61 at 2.3 A resolution is described and illustrated by Hasegawa et al. (2002), Acta Crystallogr., Sect. A, 58, C102-C102. Formaldehyde is tightly packed in a hydrophobic pocket (Met 337, Ile 301, Phe 93 and Phe 127) and is in close proximity to a zinc ion and to the NAD(H)-cofactor FDM from *P. putida* F61 has been shown to have a limited degree of substrate promiscuity (Kato et al Agric., 1983, Biol. Chem., 47(1), 39-46). The wild-type enzyme shows a weak activity toward acetyladehyde (5-10%, our results suggest even less) and methyl-glyoxal (22%)—the relative activity toward formaldehyde being 100%—, but not toward sterically more demanding substrates such as propionaldehyde, butyraldehyde, heptaldehyde, glyceraldehyde, glycolaldehyde, benzaldehyde, glyoxal or glutaraldehyde. In order to improve substrate specificity towards bulkier aldehydes—particularly acetaldehyde—we decided to modify the active pocket of FDM by substituting the large hydrophobic residues lining the active site with smaller counterparts at position 337, 301, 127 and 93. The following single-mutants have therefore been prepared and characterized:

| | | | |
|---|---|---|---|
| FDM $M^{337}A$ | FDM $I^{301}L$ | FDM $F^{127}V$ | FDM $F^{93}L$ |
| | FDM $I^{301}A$ | FDM $F^{127}A$ | FDM $F^{93}I$ |
| | FDM $I^{301}V$ | | FDM $F^{93}G$ |
| | FDM $I^{301}G$ | | FDM $F^{93}A$ |
| | FDM $I^{301}S$ | | FDM $F^{93}V$ |

Example 11

Activity of FDM Mutants Determined by pH-Stat Titration & by HPLC

Activity of FDM and its variants was assayed by pH-stat titration in a standard reaction mixture containing 20 mM formaldehyde, 100 mM KCl, 0.25 mM $KH_2PO_4$ (pH 7). The reaction was performed at RT by adding 5 μL of enzyme solution to 25 mL of standard mixture (typically 0.1-0.5 μg/mL enzyme, depending on activity). Formate formation was monitored over 5' by titration with 5 mM NaOH. One unit is defined as the amount of enzyme necessary to catalyze the formation of 1 μmol formic acid per minute. FDM $F^{93}A/I^{301}L$ (0.7 μg/mL) was the only mutant tested by pH-stat titration with 20 mM acetaldehyde instead of formaldehyde at pH 7. Given that the activity of FDM and of all single mutants on acetaldehyde is too weak to be followed by pH-stat titration, we decided to compare FDM and its variants by HPLC (Aminex HPX-87 H column, in 5 mM $H_2SO_4$, detection by RI, 0.5 mL/min). Enzymatic reactions were performed in 50 mM $KH_2PO_4$ (pH 8), 100 mM KCl and 20 mM acetaldehyde. Reactions were started by addition of FDM or of its variants (50 μg/ml). Acetaldehyde, ethanol and acetic acid were quantified in 30' intervals (retention time: acetaldehyde 21.2 min; ethanol 25.2 min; acetic acid 18.9 min). The initial reaction rates were determined (30' values) and units were calculated as the amount of enzyme needed to generate 1 μmol acetic acid in 1 min.

The results clearly show that most mutations have a deleterious effect on the specific activity toward both aldehydes. Only the $I^{301}L$ and the $F^{93}A$ turned out to have interesting properties. Introduction of leucine at position 300 led to a 2.5-fold increase in acetaldehyde activity, while the specific activity on formaldehyde increased about 10 to 20%. The $F^{92}A$ variant lost formaldehyde activity almost completely, while the specific activity with acetyladehyde increased about 3-fold compared to the wild-type enzyme and is similar to the activity of the FDM $I^{301}L$ mutant (Table 11).

TABLE 11

| | Formaldehyde pH-stat titration U/mg | Acetaldehyde HPLC U/mg |
|---|---|---|
| FDM | 150 | 0.6 |
| FDM $I^{301}L$ | 170 | 1.4 |
| FDM $I^{301}V$ | 90 | 0.4 |
| FDM $I^{301}A$ | 37 | 0.1 |
| FDM $I^{301}G$ | 8 | 0.03 |
| FDM $I^{301}S$ | 5 | n.a. |
| FDM $M^{337}A$ | 2 | 0.1 |
| FDM $F^{127}V$ | 26 | 0.1 |
| FDM $F^{127}A$ | 8 | 0.1 |
| FDM $F^{93}L$ | 4 | n.a. |
| FDM $F^{93}I$ | 2 | n.a. |
| FDM $F^{93}G$ | 2 | 0.03 |
| FDM $F^{93}A$ | 0.3 | 1.7 |
| FDM $F^{93}V$ | 1 | n.a. |
| FDM $F^{93}A/I^{301}L$ | n.a. | 2.5* |

Table 11 shows specific activities for formaldehyde (FA) and acetaldehyde (AA) of different active site mutants. FA activity was determined by pH-stat titration; AA activity was determined by HPLC, as described above. *this value is in agreement with the activity measured by pH-stat titration. n.a. not active.

Figure 2:
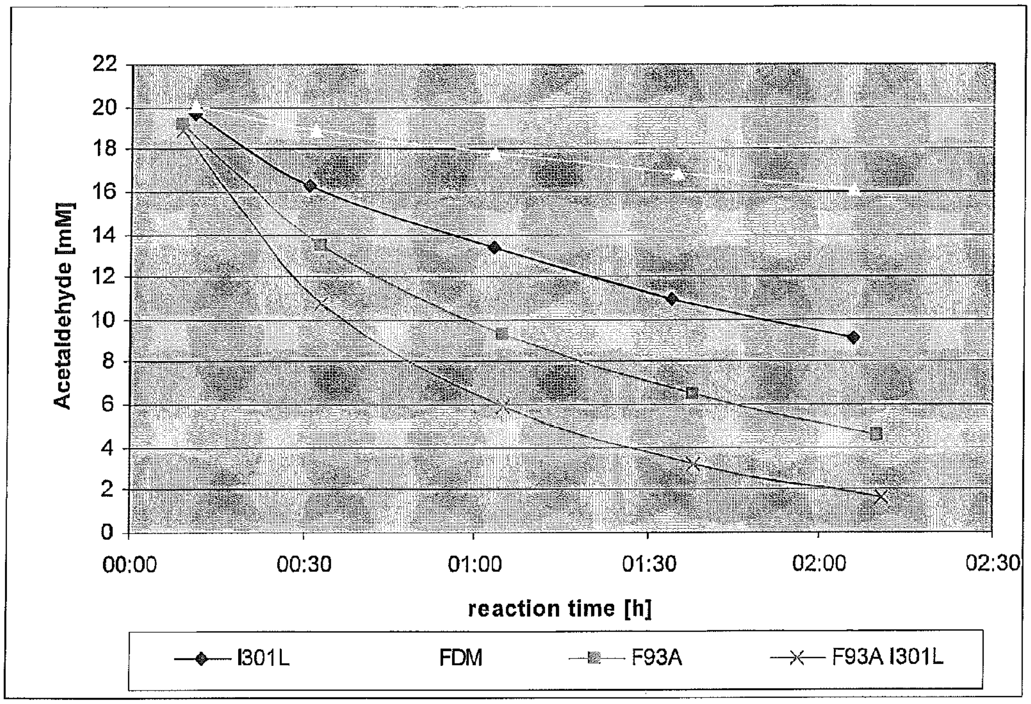
FIG. 2: Initial rates of acetaldehyde dismutation (20 mM in 50 mM $K_2HPO_4$ pH 8, 100 mM KCl) for FDM, FDM $I^{301}L$, FDM $F^{93}A$ and FDM $I^{301}L/F^{93}A$ determined by HPLC. Enzyme concentration 50 μg/mL.

The mutations at position 301 and 93 have been combined to generate the FDM $I^{301}L/F^{93}A$ variant. This double-mutant doesn't have any activity toward formaldehyde, but has a 5-fold increased activity toward acetaldehyde. Both substitutions have a synergistic effect in boosting activity with acetaldehyde (FIG. 2).

While the mutant $I^{301}L$ shows expanded substrate specificity, the FDM $F^{93}A$ variant and—especially—the double mutant exhibit a switch of substrate specificity from formaldehyde towards acetaldehyde. FIG. 3 shows the activity profile of FDM $I^{301}L$ by HPLC Example 12

Thermostability of FDM, FDM $I^{301}L$ and FDM $I^{301}L/F^{93}A$

Figure 4:
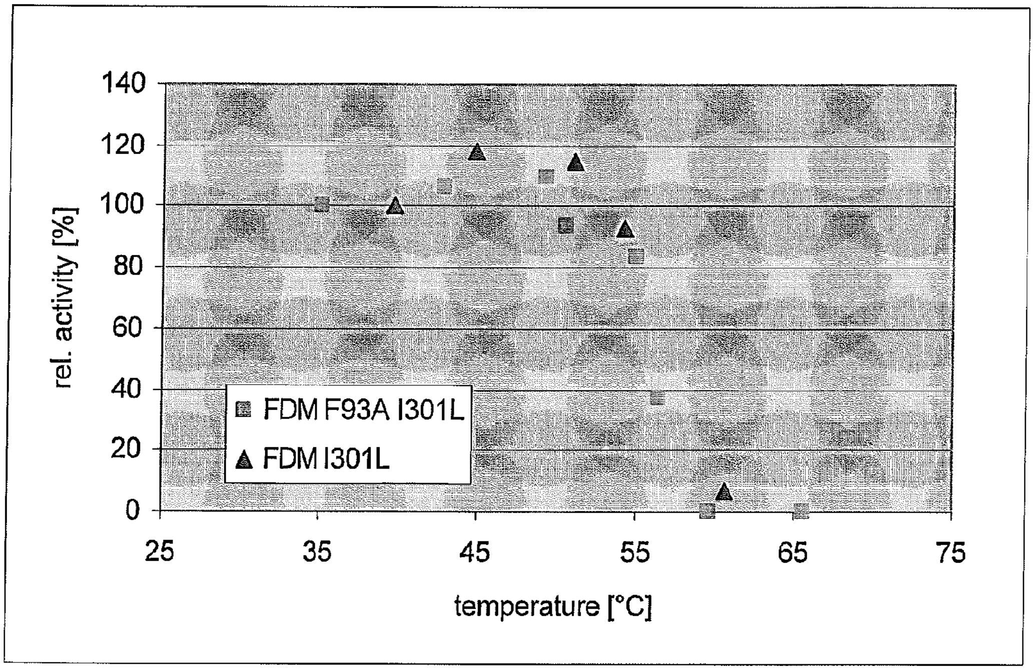
FIG. 4: Temperature-activity profile of FDM $I^{301}L$ and FDM $I^{301}L/F^{93}A$. Substrate: acetaldehyde

An important property of FDM and of its variants is the tolerance to increased temperatures both, during enzyme purification (sterilization) and during a technical application. We compared thermostability of FDM, FDM $I^{301}L$ and FDM $I^{301}L/F^{93}A$ by pre-incubating the enzyme at different temperatures for 20 min (25-65° C.) and, subsequently, by testing the sample with acetaldehyde or formaldehyde. FDM $I^{301}L$ and FDM $I^{301}L/F^{93}A$ samples were tested for acetaldehyde activity by HPLC, as described above. Data are shown as relative activities compared to the values obtained at RT (FIG. 4)

Figure 5:
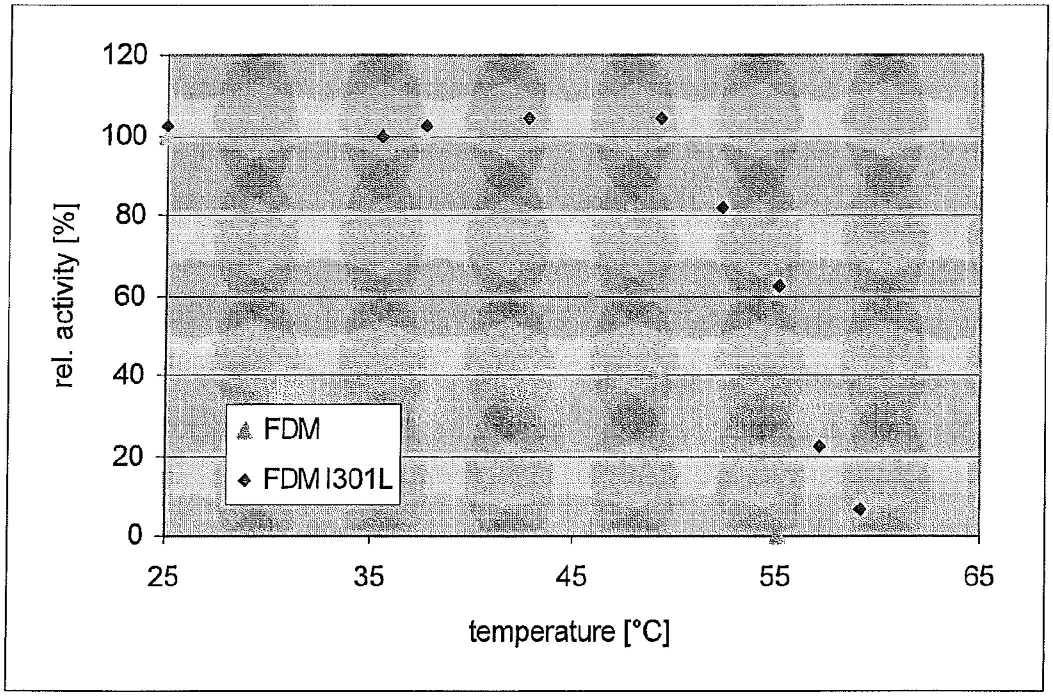
FIG. 5: Temperature-activity profile of FDM and FDM $I^{301}L$. Substrate: formaldehyde

FDM and FDM $I^{301}L$ samples were tested for formaldehyde activity by pH-stat titration, as described above. Data are shown as relative activities compared to the values obtained at RT (see FIG. 5). Interestingly, the FDM $I^{301}L$ mutant shows a clear increase in thermostability compared to the wild-type protein (+5° C., FIG. 5). The $F^{301}L$ and the $F^{301}L/F^{93}A$ mutants show the same thermostability profile on acetyladehyde ($T_{50}$ ca. 55° C.).

Example 13

Crystal Structures of FDM, FDM $I^{301}L$ and FDM $I^{301}L/F^{93}A$

Crystals of FDM $I^{301}L/F^{93}A$ and FDM $I^{301}L$ were measured at the Synchrotron SLS in Villingen, Switzerland (Table 12).

TABLE 12

Statistics of X-ray data collection

| | FDM $I^{301}L$ | FDM $I^{301}L/F^{93}A$ |
|---|---|---|
| Space group | P2 | $I4_1$ |
| Resolution range (Å) | 50-1.4 | 50-1.8 |
| Reflections | 274886 (50398) | 147396 (21502) |
| Completeness (%) | 96.8 (95.2) | 97.5 (97.4) |
| Rsym | 6.6 (66.1) | 5.7 (49.6) |
| I/σ | 11.3 (2.2) | 11.9 (2.0) |

Figure 6:
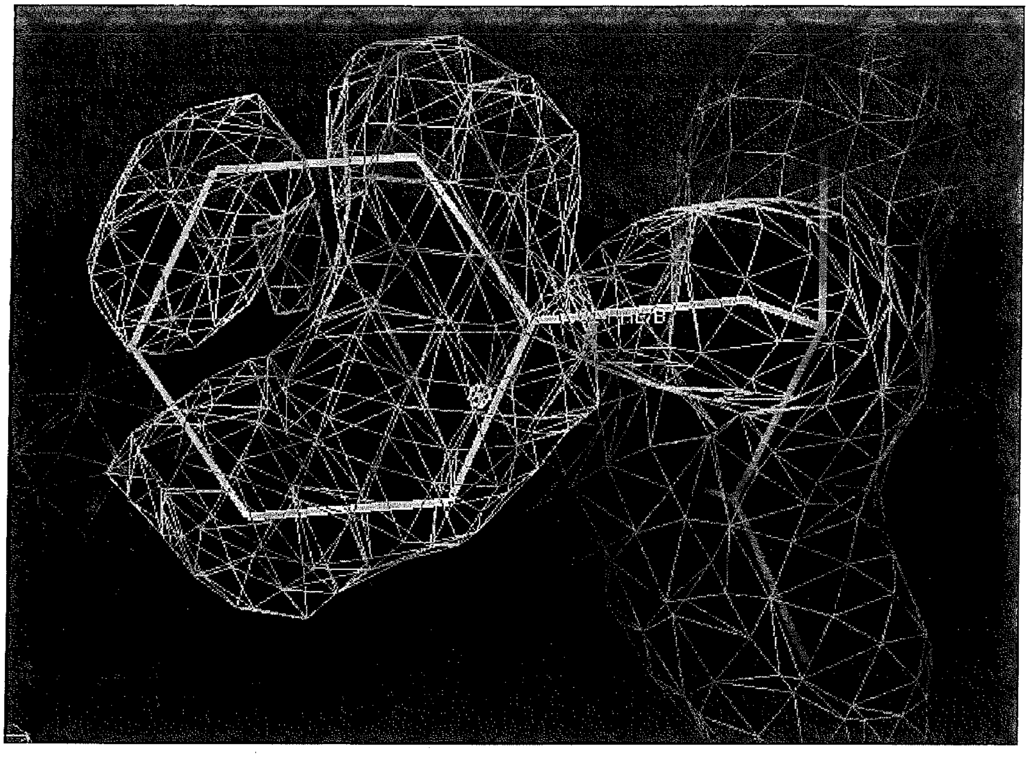
FIG. 6: The wild-type Phe 93 shown with the electron-density map of the FDM $I^{301}L/F^{93}A$ mutant.
Figure 7:
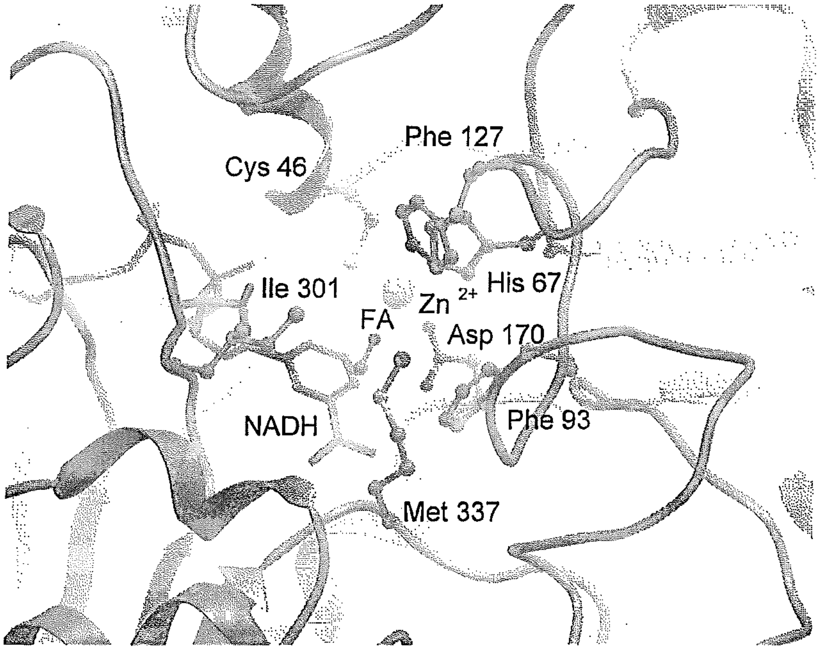
FIG. 7: Close-up of the active site of wild type FDM in complex with formaldehyde (FA)

The structure of FDM $I^{301}L/F^{93}A$ was determined by the molecular replacement method using the wild-type structure as a structural template (pdb code: 2DPH). As an example of the data quality, the wild-type phenylalanine residue at position 93 used for the structure determination is shown together with the density map of the FDM $I^{301}L/F^{93}A$ mutant (FIG. 6). The red difference electron density indicates that the phenylalanine should be modeled as an alanine and a water molecule is located at the $C_\epsilon$-position of the phenyl ring. The overall structure of the whole enzyme does not change because of the mutations. The impact of the mutations is confined to the mutagenized positions and their close neighbors. FIG. 7 shows a close-up of the active site of the wild type FDM. The protein is depicted in ribbon style. Following amino acids are shown as ball and stick: Cys 46, His 67 and Asp 170 coordinate the catalytic zinc; Ile 301 and Phe 93 are the sites where the mutations were introduced; Met 337 and Phe 127 are the amino acids which change their conformation under the influence of the mutations. The zinc ion and the cofactor (NADH) also are shown.

Figure 8:
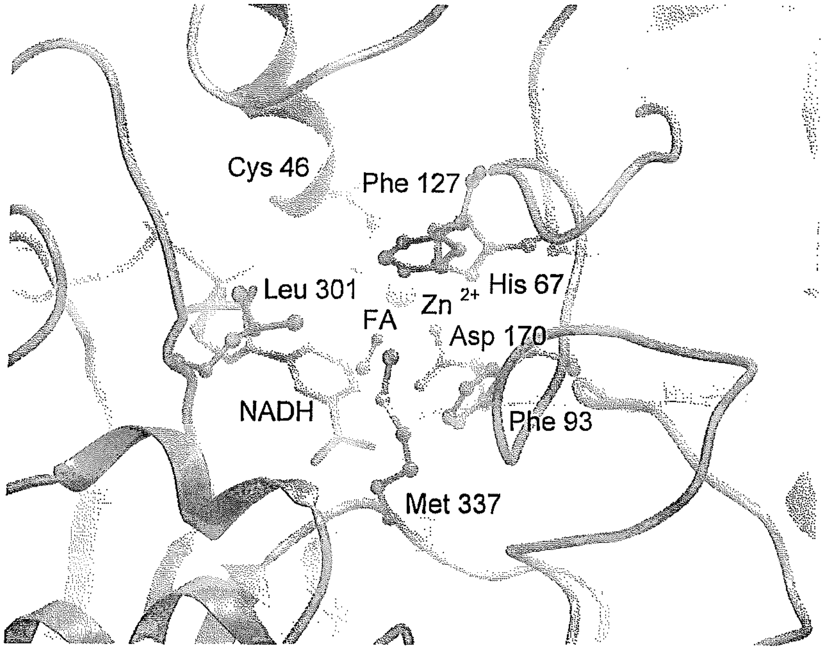
FIG. 8: Close-up of the active site of FDM $I^{301}L$ in complex with formaldehyde (FA)

Structure of the FDM $I^{301}L$ mutant:

Mutation of isoleucine 301 to leucine is clearly seen in the electron density map. The side chain adopts an orientation pointing away from the active site leading to a stronger hydrophobic contact to Val 303, Phe 265 and Phe 57. This enhanced interaction could be responsible for the increased temperature stability. The mutation has also an effect on phenylalanine 127. The whole side chain moves a little bit and phenyl ring rotates about 70° compared to the wild-type enzyme (FIG. 8). The phenyl ring is part of the substrate binding pocket and the new position of the side chain constricts the binding pocket in a way that the carbonyl group of formaldehyde and acetaldehyde is in a more favorable position for hydrid-transfer from the NADH cofactor. Moreover, the mutation of isoleucine 301 to leucine opens up the binding pocket on the opposite site allowing the sterically more demanding acetaldehyde to be better accepted as a substrate compared to the wild-type enzyme.

Figure 9:
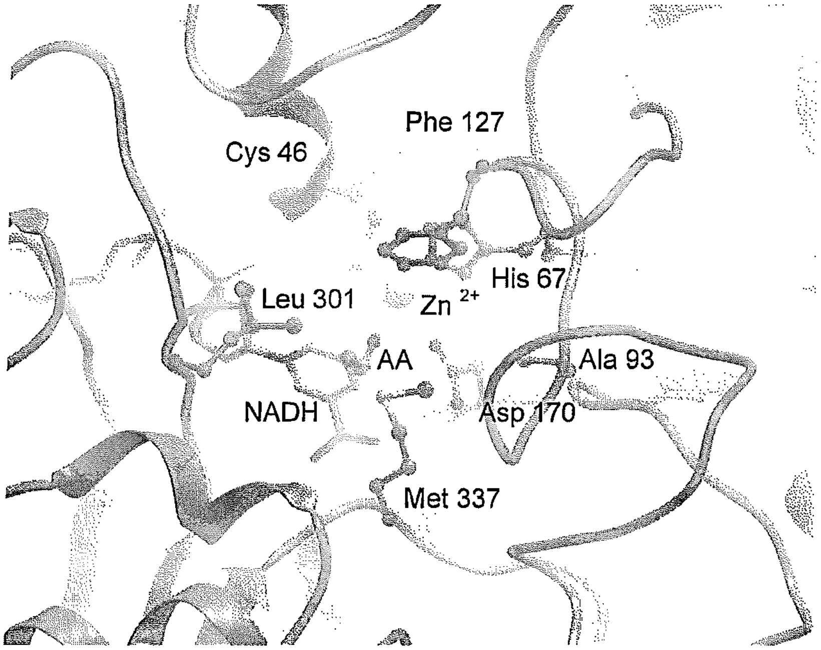
FIG. 9: Close-up of the active site of FDM $I^{301}L/F^{93}A$ in complex with acetaldehyde (AA).

Structure of the FDM $I^{301}L/F^{93}A$:

The mutation of isoleucine 301 to leucine has the same impact on Leu 301 and on Phe 127 as in the single mutant structure. The second mutation (Phe 93 to Ala) gives room for a water molecule ($H_2O$ 339) which is located near the $C_\epsilon$-position of the phenyl ring of the wild type. The water molecule is hydrogen bonded to the nicotinamide oxygen of NADH and to the carboxyl oxygen of Asp 170 which is one of the ligands of the catalytic zinc. A third weak hydrogen bond is formed with the main chain carbonyl oxygen of Ala 338. The strong hydrogen bond of the water molecule to Asp 170 distorts the conformation of the side chain and, therefore weakens the zinc coordination. In order to make the hydrogen bond, the side chain of Asp 170 has to rotate about 14° (FIG. 9). By this rotation the distance between the zinc ion and its carboxyl oxygen increases from 2.0 to 2.4 Å. The loss of the optimal zinc coordination could explain the overall reduced activity of the double mutant. Moreover, the larger active site compared to the wild-type enzyme or the I301L mutant, seem to prevent that formaldehyde can adopt a productive orientation for catalysis. This could explain the observed switch in specificity from formaldehyde to acetaldehyde. A second effect of the mutation is the altered conformation of Met 337. The $C_\epsilon$-atom of Met 337 is rotated by 90° towards the position of the former phenyl ring. This conformation is a very low energy conformation because it is the most preferred rotamer for methionines in proteins.

Overall these results suggest that the FDM $I^{301}L$ single mutant is the most preferable candidate for technical applications.

Example 14

Use of a Dry Formulation of the FDM $I^{301}L$ Mutant to Reduce the FA-Content in a Modified Anionic Polyalkylglycol-Phenol-FA Resin A further modified anionic polyalkylglycol-phenol-FA resin with a residual FA content of about 120 ppm was treated with a dry FDM $I^{301}L$ formulation (specific activity of formulation: ca. 50 U/mg). The test was performed by adding 50 mg/L of enzyme powder to the resin followed by incubation at room temperature. The following table (Table 13) shows the remaining formaldehyde (in ppm) after 5 h and after 42 days.

| | after 5 h | after 42 days |
|---|---|---|
| No enzyme | 126 ppm | 119 ppm |
| FDM $I^{301}L$ (50 mg/L) | 2 ppm | 1 ppm |

The formaldehyde content has been determined by the acetylacetone-method, as described in Example 3.

Example 15

Use of a Dry Formulation of the FDM $I^{301}L$ Mutant to Reduce the FA-Content in a Modified Beta-Naphthaline-FA Sulfonate Resin The water soluble polymer solution (modified beta-naphthaline-FA sulfonate resin) was treated with different amounts of a dry formulation of FDM $I^{301}L$ (20 to 200 mg formulation/L polymer solution) and incubated at room temperature for 5 h. At this time the same amount of enzyme was added and incubation continued for up to 11 days. The following table (Table 14) shows the remaining formaldehyde (in ppm) after 5 h, 24 h 4 days, 7 days and 11 days using 2×50 mg/L of dry enzyme formulation.

| | 5 h | 24 h | 4 d | 7 d | 11 d |
|---|---|---|---|---|---|
| No enzyme | 395 ppm | 397 ppm | 384 ppm | 386 ppm | 383 ppm |
| FDM $I^{301}L$ (2x 50 mg/L) | 278 ppm | 266 ppm | 185 ppm | 87 ppm | 50 ppm |

The formaldehyde content has been determined by the acetylacetone-method, as described in Example 3.

Example 16

Use of a Dry Formulation of the FDM $I^{301}L$ Mutant to Reduce the FA-Content in a Stabilized Anionic Acrylate Copolymer Dispersion A stabilized anionic acrylate copolymer dispersion in water (54% solid content) has been treated with 10 mg/L of the dry FDM $I^{301}L$ formulation at room temperature. After centrifugation (2-4 h at 14.000 rpm, RT), the content of formaldehyde in the clear aqueous phase was determined. The following table (Table 15) shows the formaldehyde content (in ppm) of the dispersion after 5 h, 24 h and 96 h of enzymatic treatment.

| | 5 h | 24 h | 96 h |
|---|---|---|---|
| No enzyme | 370 ppm | 310 ppm | 260 ppm |
| FDM $I^{301}L$ (10 mg/L) | 304 ppm | 170 ppm | 150 ppm |

The formaldehyde content has been determined by the acetylacetone-method, as described in Example 3.

The invention claimed is:

1. An enzyme preparation that catalyzes the degradation of formaldehyde for reducing the formaldehyde content in a formaldehyde-containing formulation, comprising an enzyme that has at least 90% sequence identity to SEQ ID NO: 2, and differs from SEQ ID NO: 2 by any of the following:

an alanine at position 93 of SEQ ID NO: 2, and/or a leucine at position 301 of SEQ ID NO: 2.

2. The enzyme preparation of claim 1 comprising an enzyme of the classification E.C.1.2.

3. The enzyme preparation of claim 1, formulated as a resin.

4. The enzyme preparation of claim 3, wherein the resin is a cross-linking agent that is a textile fabric finishing agent or a fixation agent for pigment printing.

5. The enzyme preparation claim 4, wherein the textile fabric contains cellulosic fibers.

6. The enzyme preparation of claim 5, wherein the textile fabric consists essentially of cotton.

7. The enzyme preparation of claim 3, wherein the resin is a polymer dispersant.

8. The enzyme preparation of claim 7, wherein the polymer dispersant is selected from the group consisting of naphthalene formaldehyde condensates, phenol formaldehyde condensates, urea formaldehyde condensates, melamine formaldehyde condensates and mixtures thereof.

9. An isolated polypeptide having aldehyde dismutase activity, wherein the polypeptide has at least 90% sequence identity to SEQ ID NO: 2, and differs from SEQ ID NO: 2 by any of the following:

an alanine at position 93 of SEQ ID NO: 2, and/or a leucine at position 301 of SEQ ID NO: 2 .

10. The polypeptide of claim 9, wherein the polypeptide has the amino acid sequence of SEQ ID NO: 8 or 10.

11. An isolated recombinant nucleic acid coding for a polypeptide having aldehyde dismutase activity, wherein the polypeptide has at least 90% sequence identity to SEQ ID NO: 2, and differs from SEQ ID NO: 2 by any of the following:

an alanine at position 93 of SEQ ID NO: 2, and/or a leucine at position 301 of SEQ ID NO: 2.

12. The recombinant nucleic acid of claim 11 selected from the group consisting of:

(i) the nucleic acid of SEQ ID NO: 7 or 9; and (ii) a nucleic acid encoding the polypeptide of SEQ ID NO: 8 or 10.

13. An expression cassette comprising the recombinant nucleic acid of claim 11 operably linked with at least one regulatory nucleic acid sequence.

14. A recombinant expression vector comprising the expression cassette of claim 13.

15. A recombinant microorganism carrying the expression vector of claim 14.

16. A method of preparing an isolated polypeptide having aldehyde dismutase activity, wherein the polypeptide has at least 90% sequence identity to SEQ ID NO: 2, and differs from SEQ ID NO: 2 by any of the following:

an alanine at position 93 of SEQ ID NO: 2, and/or a leucine at position 301 of SEQ ID NO: 2 , the method comprising cultivating a recombinant microorganism expressing said polypeptide, and, optionally, isolating said polypeptide from the culture.

17. The isolated polypeptide of claim 9, wherein the polypeptide reduces the aldehyde content in an aldehyde-containing formulation.

18. The polypeptide or the isolated polypeptide of claim 17, wherein the aldehyde is acetaldehyde or methylglyoxal.

19. A process for reducing the formaldehyde content in a formaldehyde-containing formulation comprising contacting the formulation with an enzyme preparation that catalyzes the degradation of formaldehyde, wherein said enzyme preparation comprises an enzyme that has at least 90% sequence identity to SEQ ID NO: 2, and differs from SEQ ID NO: 2 by any of the following:

an alanine at position 93 of SEQ ID NO: 2, and/or a leucine at position 301 of SEQ ID NO: 2.

20. The process of claim 19, wherein the formulation is a polymer dispersant or a cross-linking agent suitable for finishing a textile fabric.

21. A process for reducing the formaldehyde content in a textile fabric comprising contacting the textile fabric with an enzyme preparation that catalyzes the degradation of formaldehyde, wherein said enzyme preparation comprises an enzyme that has at least 90% sequence identity to SEQ ID NO: 2, and differs from SEQ ID NO: 2 by any of the following:

an alanine at position 93 of SEQ ID NO: 2, and/or a leucine at position 301 of SEQ ID NO: 2.

22. The process of claim 21, wherein the enzyme preparation comprises an enzyme of the classification E.C.1.2.

23. A formulation for textile-finishing comprising a cross-linking agent and an enzyme preparation that catalyzes the degradation of formaldehyde, wherein said enzyme preparation comprises an enzyme that has at least 90% sequence identity to SEQ ID NO: 2, and differs from SEQ ID NO: 2 by any of the following:

an alanine at position 93 of SEQ ID NO: 2, and/or a leucine at position 301 of SEQ ID NO: 2.

24. The formulation of claim 23, wherein the cross-linking agent is selected from the group consisting of melamine-FA, urea-FA, dimethylol dihydroxyethylene urea and derivatives thereof.

25. The formulation of claim 23, wherein the enzyme preparation comprises an enzyme of the classification E.C.1.2.

26. A formulation for treating at least one of construction materials, fiberboard, particle board, plywood, wood, leather, coatings or carpeting, the formulation containing a polymer dispersant and an enzyme preparation that catalyzes the degradation of formaldehyde, wherein said enzyme preparation comprises an enzyme that has at least 90% sequence identity to SEQ ID NO: 2, and differs from SEQ ID NO: 2 by any of the following:

an alanine at position 93 of SEQ ID NO: 2, and/or a leucine at position 301 of SEQ ID NO: 2.

27. The formulation of claim 26, wherein the polymer dispersant is selected from the group consisting of naphthalene formaldehyde condensates, phenol formaldehyde condensates, urea formaldehyde condensates, and melamine formaldehyde condensates and mixtures thereof.

28. The formulation of claim 26, wherein the enzyme preparation comprises an enzyme of the classification E.C.1.2.

* * * * *

SEQUENCE LISTING

```
<160> NUMBER OF SEQ ID NOS: 10

<210> SEQ ID NO 1
<211> LENGTH: 1740
<212> TYPE: DNA
<213> ORGANISM: Pseudomonas putida
<220> FEATURE:
<221> NAME/KEY: CDS
<222> LOCATION: (323)..(1522)

<400> SEQUENCE: 1

gagatcagca ggattatggg tgatgtggat gtaattggtt gatgtttttt gcggtctcct      60

atatggattt tataggttaa acagttgatt tggtcggctc ttttggggaa agattatttc     120

gatctttgtt aatgcctcct atatgttttc gtctaaaatg tttaattgtt ttttgcgaag     180

attagatagc ccaaaggaat tttttcaaaa aacagccttg acagggcttt gttcccgtct     240

atcatttaag ttccgtggtg cgaaaagtaa aggaagactg agcacttaaa gctagttaac     300

gttagctgaa ggggtgtttg cg atg gcc ggt aat aaa agc gtc gtc tat cat     352
                         Met Ala Gly Asn Lys Ser Val Val Tyr His
                         1               5                   10

ggg acc cgt gat ctt cgg gtt gaa aca gtt cct tat ccc aag ctt gag      400
Gly Thr Arg Asp Leu Arg Val Glu Thr Val Pro Tyr Pro Lys Leu Glu
            15                  20                  25

cac aat aat cga aag ctt gaa cat gcg gtg att tta aag gtt gta tca      448
His Asn Asn Arg Lys Leu Glu His Ala Val Ile Leu Lys Val Val Ser
        30                  35                  40

aca aat att tgt ggt tca gat caa cac att tat cgt ggg cgc ttt atc      496
Thr Asn Ile Cys Gly Ser Asp Gln His Ile Tyr Arg Gly Arg Phe Ile
    45                  50                  55
```

-continued

```
gtt cct aaa ggt cac gtg ctc ggg cac gaa att act ggg gaa gtg gta      544
Val Pro Lys Gly His Val Leu Gly His Glu Ile Thr Gly Glu Val Val
    60                  65                  70

gaa aag ggc tcg gat gtc gaa tta atg gac atc ggc gat tta gtg tct      592
Glu Lys Gly Ser Asp Val Glu Leu Met Asp Ile Gly Asp Leu Val Ser
75                  80                  85                  90

gtg cct ttt aat gtt gcg tgc ggg cgg tgc cgc aac tgt aaa gag gcg      640
Val Pro Phe Asn Val Ala Cys Gly Arg Cys Arg Asn Cys Lys Glu Ala
                95                  100                 105

cga tct gac gtt tgt gaa aat aac ctg gtc aac cca gat gcg gat tta      688
Arg Ser Asp Val Cys Glu Asn Asn Leu Val Asn Pro Asp Ala Asp Leu
            110                 115                 120

ggt gcc ttt ggc ttt gac ttg aaa ggg tgg tct ggt ggt caa gct gag      736
Gly Ala Phe Gly Phe Asp Leu Lys Gly Trp Ser Gly Gly Gln Ala Glu
        125                 130                 135

tat gtt ctt gtt cct tat gct gac tat atg ctg ctc aag ttt ggt gat      784
Tyr Val Leu Val Pro Tyr Ala Asp Tyr Met Leu Leu Lys Phe Gly Asp
    140                 145                 150

aaa gaa cag gcg atg gaa aaa ata aaa gac ctg acg ctt atc tca gat      832
Lys Glu Gln Ala Met Glu Lys Ile Lys Asp Leu Thr Leu Ile Ser Asp
155                 160                 165                 170

att cta ccg aca ggt ttt cac ggt tgc gtt tct gct gga gtg aag cca      880
Ile Leu Pro Thr Gly Phe His Gly Cys Val Ser Ala Gly Val Lys Pro
                175                 180                 185

ggt agc cat gtt tac att gca ggt gca ggt cca gta gga cgt tgt gcg      928
Gly Ser His Val Tyr Ile Ala Gly Ala Gly Pro Val Gly Arg Cys Ala
            190                 195                 200

gcg gcg ggg gcg cga ctg tta gga gcg gca tgt gtg atc gtg ggc gac      976
Ala Ala Gly Ala Arg Leu Leu Gly Ala Ala Cys Val Ile Val Gly Asp
        205                 210                 215

cag aat cct gag cgc ctg aag ctg cta tct gat gcc ggt ttt gaa acg     1024
Gln Asn Pro Glu Arg Leu Lys Leu Leu Ser Asp Ala Gly Phe Glu Thr
    220                 225                 230

atc gac tta cgt aac tct gca ccg ctg cgc gat cag att gat cag ata     1072
Ile Asp Leu Arg Asn Ser Ala Pro Leu Arg Asp Gln Ile Asp Gln Ile
235                 240                 245                 250

cta ggt aag ccg gaa gtc gac tgt ggt gta gat gcg gtt ggt ttt gaa     1120
Leu Gly Lys Pro Glu Val Asp Cys Gly Val Asp Ala Val Gly Phe Glu
                255                 260                 265

gca cat ggc ctt ggt gac gaa gct aat act gag acg cct aac ggt gcc     1168
Ala His Gly Leu Gly Asp Glu Ala Asn Thr Glu Thr Pro Asn Gly Ala
            270                 275                 280

cta aat agc ctc ttt gat gta gtc cga gca ggt ggc gca atc gga att     1216
Leu Asn Ser Leu Phe Asp Val Val Arg Ala Gly Gly Ala Ile Gly Ile
        285                 290                 295

ccg ggt att tat gta ggg agc gac cct gat cct gtt aat aaa gat gca     1264
Pro Gly Ile Tyr Val Gly Ser Asp Pro Asp Pro Val Asn Lys Asp Ala
    300                 305                 310

ggg agc gga cgc ttg cat ctt gac ttc ggc aag atg tgg aca aaa tcc     1312
Gly Ser Gly Arg Leu His Leu Asp Phe Gly Lys Met Trp Thr Lys Ser
315                 320                 325                 330

ata cgg att atg act gga atg gca cca gtg aca aac tac aat cgc cat     1360
Ile Arg Ile Met Thr Gly Met Ala Pro Val Thr Asn Tyr Asn Arg His
                335                 340                 345

ctg acc gaa gca ata ctt tgg gat caa atg cct tat ttg tcc aag gtg     1408
Leu Thr Glu Ala Ile Leu Trp Asp Gln Met Pro Tyr Leu Ser Lys Val
            350                 355                 360

atg aat att gaa gtg att aca ctt gat caa gca ccg gat ggg tat gcg     1456
Met Asn Ile Glu Val Ile Thr Leu Asp Gln Ala Pro Asp Gly Tyr Ala
        365                 370                 375
```

-continued

```
aaa ttc gat aag ggg tct ccc gct aag ttt gtt atc gat ccg cat ggc     1504
Lys Phe Asp Lys Gly Ser Pro Ala Lys Phe Val Ile Asp Pro His Gly
    380                 385                 390

atg ttg aag aat aaa tga gctagcattt gaggtgtttc gcgaatggcg           1552
Met Leu Lys Asn Lys
395

atgctctggc agtattgtta acgggctaaa atgagtgttt tgtagtgagt gaaagcctgc   1612

cccactaaat ttgtggggca ggccgtaaga tccaggtgct cgcaccgttc agtcattcat   1672

actacccata gaactgccgc tccctaatta cctgggagag gcaaggctct tgacaagcag   1732

ggccttta                                                            1740
```

<210> SEQ ID NO 2
<211> LENGTH: 399
<212> TYPE: PRT
<213> ORGANISM: Pseudomonas putida

<400> SEQUENCE: 2

```
Met Ala Gly Asn Lys Ser Val Val Tyr His Gly Thr Arg Asp Leu Arg
1               5                   10                  15

Val Glu Thr Val Pro Tyr Pro Lys Leu Glu His Asn Asn Arg Lys Leu
            20                  25                  30

Glu His Ala Val Ile Leu Lys Val Val Ser Thr Asn Ile Cys Gly Ser
        35                  40                  45

Asp Gln His Ile Tyr Arg Gly Arg Phe Ile Val Pro Lys Gly His Val
    50                  55                  60

Leu Gly His Glu Ile Thr Gly Glu Val Val Glu Lys Gly Ser Asp Val
65                  70                  75                  80

Glu Leu Met Asp Ile Gly Asp Leu Val Ser Val Pro Phe Asn Val Ala
                85                  90                  95

Cys Gly Arg Cys Arg Asn Cys Lys Glu Ala Arg Ser Asp Val Cys Glu
            100                 105                 110

Asn Asn Leu Val Asn Pro Asp Ala Asp Leu Gly Ala Phe Gly Phe Asp
        115                 120                 125

Leu Lys Gly Trp Ser Gly Gly Gln Ala Glu Tyr Val Leu Val Pro Tyr
    130                 135                 140

Ala Asp Tyr Met Leu Leu Lys Phe Gly Asp Lys Glu Gln Ala Met Glu
145                 150                 155                 160

Lys Ile Lys Asp Leu Thr Leu Ile Ser Asp Ile Leu Pro Thr Gly Phe
                165                 170                 175

His Gly Cys Val Ser Ala Gly Val Lys Pro Gly Ser His Val Tyr Ile
            180                 185                 190

Ala Gly Ala Gly Pro Val Gly Arg Cys Ala Ala Ala Gly Ala Arg Leu
        195                 200                 205

Leu Gly Ala Ala Cys Val Ile Val Gly Asp Gln Asn Pro Glu Arg Leu
    210                 215                 220

Lys Leu Leu Ser Asp Ala Gly Phe Glu Thr Ile Asp Leu Arg Asn Ser
225                 230                 235                 240

Ala Pro Leu Arg Asp Gln Ile Asp Gln Ile Leu Gly Lys Pro Glu Val
                245                 250                 255

Asp Cys Gly Val Asp Ala Val Gly Phe Glu Ala His Gly Leu Gly Asp
            260                 265                 270

Glu Ala Asn Thr Glu Thr Pro Asn Gly Ala Leu Asn Ser Leu Phe Asp
        275                 280                 285
```

-continued

```
Val Val Arg Ala Gly Gly Ala Ile Gly Ile Pro Gly Ile Tyr Val Gly
    290                 295                 300

Ser Asp Pro Asp Pro Val Asn Lys Asp Ala Gly Ser Gly Arg Leu His
305                 310                 315                 320

Leu Asp Phe Gly Lys Met Trp Thr Lys Ser Ile Arg Ile Met Thr Gly
                325                 330                 335

Met Ala Pro Val Thr Asn Tyr Asn Arg His Leu Thr Glu Ala Ile Leu
            340                 345                 350

Trp Asp Gln Met Pro Tyr Leu Ser Lys Val Met Asn Ile Glu Val Ile
        355                 360                 365

Thr Leu Asp Gln Ala Pro Asp Gly Tyr Ala Lys Phe Asp Lys Gly Ser
    370                 375                 380

Pro Ala Lys Phe Val Ile Asp Pro His Gly Met Leu Lys Asn Lys
385                 390                 395


<210> SEQ ID NO 3
<211> LENGTH: 1197
<212> TYPE: DNA
<213> ORGANISM: Artificial
<220> FEATURE:
<223> OTHER INFORMATION: Codon-optimized DNA sequence for FDM from
      Pseudomonas putida F61

<400> SEQUENCE: 3

atggcgggta ataaatcggt ggtgtatcat ggtacccgcg acctgcgtgt tgaaaccgtg      60

ccgtatccga agctggaaca taacaaccgt aaactggaac acgcagttat ccttaaagtt     120

gtgagcacca acatttgtgg tagcgatcag catatttacc gcggccgctt tattgtgccg     180

aaaggccatg ttttaggcca cgaaattacc ggcgaagtcg tggaaaaagg cagtgatgtt     240

gaactgatgg atattggcga tctggtatcc gtgccgttta acgtcgcgtg cggtcgttgc     300

cggaactgta aggaagcccg cagcgatgtg tgcgaaaaca atcttgtgaa ccccgatgcg     360

gatctgggtg cgtttggctt tgatctgaaa gggtggagcg gaggtcaagc ggagtacgtt     420

ctcgtgcctt atgcggatta catgctgctg aaatttggcg ataaagagca agccatggaa     480

aaaattaaag atctgaccct gatctcggat atcctgccaa cgggttttca tggctgcgtt     540

tctgccggtg ttaagcctgg cagccatgtc tatattgcgg gcgcaggtcc agtcggtcgc     600

tgtgcagccg cgggtgcgcg cctgctgggc gccgcatgcg tgatcgtggg ggaccagaac     660

ccggagcgtc tcaaactgtt gtctgatgcc ggctttgaaa ccattgactt acgcaatagt     720

gcgccgctgc gtgatcagat cgatcagatc ttaggcaaac cggaagtgga ctgcggcgtg     780

gatgcggtgg gcttcgaagc acatggctta ggtgatgaag ccaatactga gacgccgaac     840

ggcgccctga acagcttgtt cgacgtggtg cgcgctgggg gcgctattgg tattccgggt     900

atttatgtcg ggtctgatcc ggatccggtg aacaaagatg ccggctccgg ccgcctgcac     960

ttggatttcg gcaaaatgtg gaccaaatcc attcgtatca tgacggggat ggcgccagtt    1020

actaattata accgtcatct gacggaagcg attctgtggg accagatgcc gtatctgtcg    1080

aaagtaatga acatcgaagt tattaccctg gaccaggcgc cggatggtta tgcgaaattt    1140

gataaaggca gtccggcgaa atttgtgatt gatccacatg gcatgttgaa aaataaa       1197


<210> SEQ ID NO 4
<211> LENGTH: 4535
<212> TYPE: DNA
<213> ORGANISM: Artificial
<220> FEATURE:
<223> OTHER INFORMATION: Plasmid pDHE-FDM
```

```
<220> FEATURE:
<221> NAME/KEY: Promoter
<222> LOCATION: (393)..(482)
<220> FEATURE:
<221> NAME/KEY: GroES
<222> LOCATION: (509)..(802)
<220> FEATURE:
<221> NAME/KEY: GroEL
<222> LOCATION: (846)..(2489)

<400> SEQUENCE: 4

gacgtctgtg tggaattgtg agcggataac aatttcacac agggccctcg gacaccgagg     60

agaatgtcaa gaggcgaaca cacaacgtct tggagcgcca gaggaggaac gagctaaaac    120

ggagcttttt tgccctgcgt gaccagatcc cggagttgga aaacaatgaa aaggcccccca    180

aggtagttat ccttaaaaaa gccacagcat acatcctgtc cgtccaagca gaggagcaaa    240

agctcatttc tgaagaggac ttgttgcgga aacgacgaga acagttgaaa cacaaacttg    300

aacagctacg gaactcttgt gcgtaaggaa aagtaaggaa aacgattcct tctaacagaa    360

atgtcctgag caatcaccta tgaactgtcg actcgagaaa atttatcaaa aagagtgttg    420

acttgtgagc ggataacaat gatacttaga ttcaattgtg agcggataac aatttcacac    480

agaattcatt aaagaggaga aattaaccat gaatattcgt ccattgcatg atcgcgtgat    540

cgtcaagcgt aaagaagttg aaactaaatc tgctggcggc atcgttctga ccggctctgc    600

agcggctaaa tccacccgcg gcgaagtgct ggctgtcggc aatggccgta tccttgaaaa    660

tggcgaagtg aagccgctgg atgtgaaagt tggcgacatc gttattttca acgatggcta    720

cggtgtgaaa tctgagaaga tcgacaatga agaagtgttg atcatgtccg aaagcgacat    780

tctggcaatt gttgaagcgt aatccgcgca cgacactgaa catacgaatt taaggaataa    840

agataatggc agctaaagac gtaaaattcg gtaacgacgc tcgtgtgaaa atgctgcgcg    900

gcgtaaacgt actggcagat gcagtgaaag ttaccctcgg tccaaaaggc cgtaacgtag    960

ttctggataa atctttcggt gcaccgacca tcaccaaaga tggtgtttcc gttgctcgtg   1020

aaatcgaact ggaagacaag ttcgaaaata tgggtgcgca gatggtgaaa gaagttgcct   1080

ctaaagcaaa cgacgctgca ggcgacggta ccaccactgc aaccgtactg gctcaggcta   1140

tcatcactga aggtctgaaa gctgttgctg cgggcatgaa cccgatggac ctgaaacgtg   1200

gtatcgacaa agcggttacc gctgcagttg aagaactgaa agcgctgtcc gtaccatgct   1260

ctgactctaa agcgattgct caggttggta ccatctccgc taactccgac gaaaccgtag   1320

gtaaactgat cgctgaagcg atggacaaag tcggtaaaga aggcgttatc accgttgaag   1380

acggtaccgg tctgcaggac gaactggacg tggttgaagg tatgcagttc gaccgtggct   1440

acctgtctcc ttacttcatc aacaagccgg aaactggcgc agtagaactg gaaagcccgt   1500

tcatcctgct ggctgacaag aaaatctcca acatccgcga aatgctgccg gttctggaag   1560

ctgttgccaa agcaggcaaa ccgctgctga tcatcgctga agatgtagaa ggcgaagcgc   1620

tggcaactgc tgttgttaac accattcgtg gcatcgtgaa agtcgctgcg gttaaagcac   1680

cgggcttcgg cgatcgtcgt aaagctatgc tgcaggatat cgcaaccctg actggcggta   1740

ccgtgatctc tgaagagatc ggtatggagc tggaaaaagc aaccctggaa gacctgggtc   1800

aggctaaacg tgttgtgatc aacaaagaca ccaccactat catcgatggc gtgggtgaag   1860

aagctgcaat ccagggccgt gttgctcaga tccgtcagca gattgaagaa gcaacttctg   1920

actacgaccg tgaaaaactg caggaacgcg tagcgaaact ggcaggcggc gttgcagtta   1980

tcaaagtggg tgctgctacc gaagttgaaa tgaaagagaa aaaagcacgc gttgaagatg   2040
```

-continued

```
ccctgcacgc gacccgtgct gcggtagaag aaggcgtggt tgctggtggt ggtgttgcgc   2100
tgatccgcgt agcgtctaaa ctggctgacc tgcgtggtca gaacgaagac cagaacgtgg   2160
gtatcaaagt tgcactgcgt gcaatggaag ctccgctgcg tcagatcgta ttgaactgcg   2220
gcgaagaacc gtctgttgtt gctaacaccg ttaaaggcgg cgacggcaac tacggttaca   2280
acgcagcaac cgaagaatac ggcaacatga tcgacatggg tatcctggat ccaaccaaag   2340
taactcgttc tgctctgcag tacgcagctt ctgtggctgg cctgatgatc accaccgaat   2400
gcatggttac cgacctgccg aaaaacgatg cagctgactt aggcgctgct ggcggtatgg   2460
gcggcatggg tggcatgggc ggcatgatgt aacctagggg atatattccg cttcctcgct   2520
cactgactcg ctacgctcgg tcgttcgact gcggcgagcg gaaatggctt acgaacgggg   2580
cggagatttc ctggaagatg ccaggaagat acttaacagg gaagtgagag ggccgcggca   2640
aagccgtttt tccataggct ccgcccccct gacaagcatc acgaaatctg acgctcaaat   2700
cagtggtggc gaaacccgac aggactataa agataccagg cgtttccccc tggcggctcc   2760
ctcgtgcgct ctcctgttcc tgcctttcgg tttaccggtg tcattccgct gttatggccg   2820
cgtttgtctc attccacgcc tgacactcag ttccgggtag gcagttcgct ccaagctgga   2880
ctgtatgcac gaaccccccg ttcagtccga ccgctgcgcc ttatccggta actatcgtct   2940
tgagtccaac ccggaaagac atgcaaaagc accactggca gcagccactg gtaattgatt   3000
tagaggagtt agtcttgaag tcatgcgccg gttaaggcta aactgaaagg acaagttttg   3060
gtgactgcgc tcctccaagc cagttacctc ggttcaaaga gttggtagct cagagaacct   3120
tcgaaaaacc gccctgcaag gcggtttttt cgttttcaga gcaagagatt acgcgcagac   3180
caaaacgatc tcaagaagat catcttatta atcagataaa atatttctag atttcagtgc   3240
aatttatctc ttcaaatgta gcacctgaag tcagccccat acgatataag ttgttactag   3300
tgcttggatt ctcaccaata aaaaacgccc ggcggcaacc gagcgttctg aacaaatcca   3360
gatggagttc tgaggtcatt actggatcta tcaacaggag tccaagcgag ctcgatatcc   3420
gtcggcttga acgaattgtt agacattatt tgccgactac cttggtgatc tcgcctttca   3480
cgtagtggac aaattcttcc aactgatctg cgcgcgaggc caagcgatct tcttcttgtc   3540
caagataagc ctgtctagct tcaagtatga cgggctgata ctgggccggc aggcgctcca   3600
ttgcccagtc ggcagcgaca tccttcggcg cgattttgcc ggttactgcg ctgtaccaaa   3660
tgcgggacaa cgtaagcact acatttcgct catcgccagc ccagtcgggc ggcgagttcc   3720
atagcgttaa ggtttcattt agcgcctcaa atagatcctg ttcaggaacc ggatcaaaga   3780
gttcctccgc cgctggacct accaaggcaa cgctatgttc tcttgctttt gtcagcaaga   3840
tagccagatc aatgtcgtac gtggctggct cgaagatacc tgcaagaatg tcattgcgct   3900
gccattctcc aaattgcagt tcgcgcttag ctggataacg ccacggaatg atgtcgtcgt   3960
gcacaacaat ggtgacttct acagcgcgga gaatctcgct ctctccaggg gaagccgaag   4020
tttccaaaag gtcgttgatc aaagctcgcc gcgttgtttc atcaagcctt acggtcaccg   4080
taaccagcaa atcaatatca ctgtgtggct tcaggccgcc atccactgcg gagccgtaca   4140
aatgtacggc cagcaacgtc ggttcgagat ggcgctcgat gacgccaact acctctgata   4200
gttgagtcga tacttcggcg atcaccgctt ccctcatgat gtttaacttt gttttagggc   4260
gactgccctg ctgcgtaaca tcgttgctgc tccataacat caaacatcga cccacggcgt   4320
aacgcgcttg ctgcttggat gcccgaggca tagactgtac cccaaaaaaa catgtcataa   4380
caagaagcca tgaaaaccgc cactgcgccg ttaccaccgc tgcgttcggt caaggttgtg   4440
```

-continued gaccagttgc gtgacggcag ttacgctact tgcattacag cttacgaacc gaacgaggct 4500
tatgtccact gggttcgtgc cttcatccgg atatc 4535

<210> SEQ ID NO 5
<211> LENGTH: 5473
<212> TYPE: DNA
<213> ORGANISM: Artificial
<220> FEATURE:
<223> OTHER INFORMATION: Plasmid pAgro
<220> FEATURE:
<221> NAME/KEY: Promoter-Part2
<222> LOCATION: (1)..(33)
<220> FEATURE:
<221> NAME/KEY: CDS Dismutase
<222> LOCATION: (59)..(1255)
<220> FEATURE:
<221> NAME/KEY: Promoter-Part1
<222> LOCATION: (5360)..(5473)

<400> SEQUENCE: 5
aattcaggcg ctttttagac tggtcgtaat gaacaattct taagaaggag atatacatat 60
ggcgggtaat aaatcggtgg tgtatcatgg tacccgcgac ctgcgtgttg aaaccgtgcc 120
gtatccgaag ctggaacata acaaccgtaa actggaacac gcagttatcc ttaaagttgt 180
gagcaccaac atttgtggta gcgatcagca tatttaccgc ggccgcttta ttgtgccgaa 240
aggccatgtt ttaggccacg aaattaccgg cgaagtcgtg gaaaaaggca gtgatgttga 300
actgatggat attggcgatc tggtatccgt gccgtttaac gtcgcgtgcg gtcgttgccg 360
gaactgtaag gaagcccgca gcgatgtgtg cgaaaacaat cttgtgaacc ccgatgcgga 420
tctgggtgcg tttggctttg atctgaaagg gtggagcgga ggtcaagcgg agtacgttct 480
cgtgccttat gcggattaca tgctgctgaa atttggcgat aaagagcaag ccatggaaaa 540
aattaaagat ctgaccctga tctcggatat cctgccaacg ggttttcatg gctgcgtttc 600
tgccggtgtt aagcctggca gccatgtcta tattgcgggc gcaggtccag tcggtcgctg 660
tgcagccgcg ggtgcgcgcc tgctgggcgc cgcatgcgtg atcgtggggg accagaaccc 720
ggagcgtctc aaactgttgt ctgatgccgg ctttgaaacc attgacttac gcaatagtgc 780
gccgctgcgt gatcagatcg atcagatctt aggcaaaccg gaagtggact gcggcgtgga 840
tgcggtgggc ttcgaagcac atggcttagg tgatgaagcc aatactgaga cgccgaacgg 900
cgccctgaac agcttgttcg acgtggtgcg cgctgggggc gctattggta ttccgggtat 960
ttatgtcggg tctgatccgg atccggtgaa caaagatgcc ggctccggcc gcctgcactt 1020
ggatttcggc aaaatgtgga ccaaatccat tcgtatcatg acggggatgg cgccagttac 1080
taattataac cgtcatctga cggaagcgat tctgtgggac cagatgccgt atctgtcgaa 1140
agtaatgaac atcgaagtta ttaccctgga ccaggcgccg gatggttatg cgaaatttga 1200
taaaggcagt ccggcgaaat ttgtgattga tccacatggc atgttgaaaa ataaataaaa 1260
gcttggctgt tttggcggat gagagaagat tttcagcctg atacagatta aatcagaacg 1320
cagaagcggt ctgataaaac agaatttgcc tggcggcagt agcgcggtgg tcccacctga 1380
ccccatgccg aactcagaag tgaaacgccg tagcgccgat ggtagtgtgg ggtctcccca 1440
tgcgagagta gggaactgcc aggcatcaaa taaaacgaaa ggctcagtcg aaagactggg 1500
cctttcgttt tatctgttgt ttgtcggtga acgctctcct gagtaggaca aatccgccgg 1560
gagcggattt gaacgttgcg aagcaacggc ccggagggtg gcgggcagga cgcccgccat 1620
aaactgccag gcatcaaatt aagcagaagg ccatcctgac ggatggcctt tttgcgtttc 1680

-continued

```
tacaaactct tttgtttatt tttctaaata cattcaaata tgtatccgct catgagacaa   1740
taaccctgat aaatgcttca ataatattga aaaaggaaga gtatgagtat tcaacatttc   1800
cgtgtcgccc ttattccctt ttttgcggca ttttgccttc ctgtttttgc tcacccagaa   1860
acgctggtga aagtaaaaga tgctgaagat cagttgggtg cacgagtggg ttacatcgaa   1920
ctggatctca acagcggtaa gatccttgag agttttcgcc ccgaagaacg ttttccaatg   1980
atgagcactt ttaaagttct gctatgtggc gcggtattat cccgtgttga cgccgggcaa   2040
gagcaactcg gtcgccgcat acactattct cagaatgact tggttgagta ctcaccagtc   2100
acagaaaagc atcttacgga tggcatgaca gtaagagaat tatgcagtgc tgccataacc   2160
atgagtgata acactgcggc caacttactt ctgacaacga tcggaggacc gaaggagcta   2220
accgcttttt tgcacaacat gggggatcat gtaactcgcc ttgatcgttg ggaaccggag   2280
ctgaatgaag ccataccaaa cgacgagcgt gacaccacga tgcctgtagc aatggcaaca   2340
acgttgcgca aactattaac tggcgaacta cttactctag cttcccggca acaattaata   2400
gactggatgg aggcggataa agttgcagga ccacttctgc gctcggccct tccggctggc   2460
tggtttattg ctgataaatc tggagccggt gagcgtgggt ctcgcggtat cattgcagca   2520
ctggggccag atggtaagcc ctcccgtatc gtagttatct acacgacggg gagtcaggca   2580
actatggatg aacgaaatag acagatcgct gagataggtg cctcactgat taagcattgg   2640
taactgtcag accaagttta ctcatatata ctttagattg atttaaaact tcatttttaa   2700
tttaaaagga tctaggtgaa gatccttttt gataatctca tgaccaaaat cccttaacgt   2760
gagttttcgt tccactgagc gtcagacccc gtagaaaaga tcaaaggatc ttcttgagat   2820
cctttttttc tgcgcgtaat ctgctgcttg caaacaaaaa aaccaccgct accagcggtg   2880
gtttgtttgc cggatcaaga gctaccaact ctttttccga aggtaactgg cttcagcaga   2940
gcgcagatac caaatactgt ccttctagtg tagccgtagt taggccacca cttcaagaac   3000
tctgtagcac cgcctacata cctcgctctg ctaatcctgt taccagtggc tgctgccagt   3060
ggcgataagt cgtgtcttac cgggttggac tcaagacgat agttaccgga taaggcgcag   3120
cggtcgggct gaacgggggg ttcgtgcaca cagcccagct tggagcgaac gacctacacc   3180
gaactgagat acctacagcg tgagctatga gaaagcgcca cgcttcccga agggagaaag   3240
gcggacaggt atccggtaag cggcagggtc ggaacaggag agcgcacgag ggagcttcca   3300
gggggaaacg cctggtatct ttatagtcct gtcgggtttc gccacctctg acttgagcgt   3360
cgatttttgt gatgctcgtc aggggggcgg agcctatgga aaaacgccag caacgcggcc   3420
tttttacggt tcctggcctt ttgctggcct tttgctcaca tgttctttcc tgcgttatcc   3480
cctgattctg tggataaccg tattaccgcc tttgagtgag ctgataccgc tcgccgcagc   3540
cgaacgaccg agcgcagcga gtcagtgagc gaggaagcgg aagagcgcct gatgcggtat   3600
tttctcctta cgcatctgtg cggtatttca caccgcatat atggtgcact ctcagtacaa   3660
tctgctctga tgccgcatag ttaagccagt atacactccg ctatcgctac gtgactgggt   3720
catggctgcg ccccgacacc cgccaacacc cgctgacgcg ccctgacggg cttgtctgct   3780
cccggcatcc gcttacagac aagctgtgac cgtctccggg agctgcatgt gtcagaggtt   3840
ttcaccgtca tcaccgaaac gcgcgaggca gctgcggtaa agctcatcag cgtggtcgtg   3900
aagcgattca cagatgtctg cctgttcatc cgcgtccagc tcgttgagtt tctccagaag   3960
cgttaatgtc tggcttctga taaagcgggc catgttaagg gcggtttttt cctgtttggt   4020
cactgatgcc tccgtgtaag ggggatttct gttcatgggg gtaatgatac cgatgaaacg   4080
```

-continued agagaggatg ctcacgatac gggttactga tgatgaacat gcccggttac tggaacgttg 4140
tgagggtaaa caactggcgg tatggatgcg gcgggaccag agaaaaatca ctcagggtca 4200
atgccagcgc ttcgttaata cagatgtagg tgttccacag ggtagccagc agcatcctgc 4260
gatgcagatc cggaacataa tggtgcaggg cgctgacttc cgcgtttcca gactttacga 4320
aacacggaaa ccgaagacca ttcatgttgt tgctcaggtc gcagacgttt tgcagcagca 4380
gtcgcttcac gttcgctcgc gtatcggtga ttcattctgc taaccagtaa ggcaaccccg 4440
ccagcctagc cgggtcctca acgacaggag cacgatcatg cgcacccgtg gccaggaccc 4500
aacgctgccc gagatgcgcc gcgtgcggct gctggagatg gcggacgcga tggatatgtt 4560
ctgccaaggg ttggtttgcg cattcacagt tctccgcaag aattgattgg ctccaattct 4620
tggagtggtg aatccgttag cgaggtgccg ccggcttcca ttcaggtcga ggtggcccgg 4680
ctccatgcac cgcgacgcaa cgcggggagg cagacaaggt atagggcggc gcctacaatc 4740
catgccaacc cgttccatgt gctcgccgag gcggcataaa tcgccgtgac gatcagcggt 4800
ccaatgatcg aagttaggct ggtaagagcc gcgagcgatc cttgaagctg tccctgatgg 4860
tcgtcatcta cctgcctgga cagcatggcc tgcaacgcgg gcatcccgat gccgccggaa 4920
gcgagaagaa tcataatggg gaaggccatc cagcctcgcg tcgcgaacgc cagcaagacg 4980
tagcccagcg cgtcggccgc catgccggcg ataatggcct gcttctcgcc gaaacgtttg 5040
gtggcgggac cagtgacgaa ggcttgagcg agggcgtgca agattccgaa taccgcaagc 5100
gacaggccga tcatcgtcgc gctccagcga aagcggtcct cgccgaaaat gacccagagc 5160
gctgccggca cctgtcctac gagttgcatg ataaagaaga cagtcataag tgcggcgacg 5220
atagtcatgc cccgcgccca ccggaaggag ctgactgggt tgaaggctct caagggcatc 5280
ggtcgacgct ctcccttatg cgactcctgc attaggaagc agcccagtag taggttgagg 5340
ccgttgagca ccgccgccgc aaggaatggt gcatgcatcg atcaccacaa ttcagcaaat 5400
tgtgaacatc atcacgttca tctttccctg gttgccaatg gcccattttc ctgtcagtaa 5460
cgagaaggtc gcg 5473

<210> SEQ ID NO 6
<211> LENGTH: 4945
<212> TYPE: DNA
<213> ORGANISM: Artificial
<220> FEATURE:
<223> OTHER INFORMATION: Plasmid pHSG
<220> FEATURE:
<221> NAME/KEY: Repressor LacI
<222> LOCATION: (147)..(1235)

<400> SEQUENCE: 6
atgaccatga ttacgaattc tgtgtgaaat tgttatccgc tcacaattga atctaagtat 60
cattgttatc cgctcacaag tcaacactct tttgataaa ttttctcgac aattcgcgct 120
aacttacatt aattgcgttg cgctcactgc ccgctttcca gtcgggaaac ctgtcgtgcc 180
agctgcatta atgaatcggc caacgcgcgg ggagaggcgg tttgcgtatt gggcgccagg 240
gtggtttttc ttttcaccag tgagacgggc aacagctgat tgcccttcac cgcctggccc 300
tgagagagtt gcagcaagcg gtccacgctg gtttgcccca gcaggcgaaa atcctgtttg 360
atggtggtta acggcgggat ataacatgag ctgtcttcgg tatcgtcgta tcccactacc 420
gagatatccg caccaacgcg cagcccggac tcggtaatgg cgcgcattgc gcccagcgcc 480
atctgatcgt tggcaaccag catcgcagtg ggaacgatgc cctcattcag catttgcatg 540

```
gtttgttgaa aaccggacat ggcactccag tcgccttccc gttccgctat cggctgaatt    600
tgattgcgag tgagatattt atgccagcca gccagacgca gacgcgccga gacagaactt    660
aatgggcccg ctaacagcgc gatttgctgg tgacccaatg cgaccagatg ctccacgccc    720
agtcgcgtac cgtcttcatg ggagaaaata atactgttga tgggtgtctg gtcagagaca    780
tcaagaaata acgccggaac attagtgcag gcagcttcca cagcaatggc atcctggtca    840
tccagcggat agttaatgat cagcccactg acgcgttgcg cgagaagatt gtgcaccgcc    900
gctttacagg cttcgacgcc gcttcgttct accatcgaca ccaccacgct ggcacccagt    960
tgatcggcgc gagatttaat cgccgcgaca atttgcgacg gcgcgtgcag ggccagactg   1020
gaggtggcaa cgccaatcag caacgactgt ttgcccgcca gttgttgtgc cacgcggttg   1080
ggaatgtaat tcagctccgc catcgccgct tccacttttt cccgcgtttt cgcagaaacg   1140
tggctggcct ggttcaccac gcgggaaacg gtctgataag agacaccggc atactctgcg   1200
acatcgtata acgttactgg tttcacattc accaccctga attgactctc ttccgggcgc   1260
tatcatgcca taccgcgaaa ggttttgcac cattcgatgg tgtcaacgta aatgcatgcc   1320
gcttcgcctt cgcgcgcgaa ttgtcgagtc gacctgcagc caagcttggc actggccgtc   1380
gttttacaac gtcgtgactg ggaaaaccct ggcgttaccc aacttaatcg ccttgcagca   1440
catccccctt tcgccagctg gcgtaatagc gaagaggccc gcaccgatcg cccttcccaa   1500
cagttgcgca gcctgaatgg cgaatggcgc taaccgtttt tatcaggctc tgggaggcag   1560
aataaatgat catatcgtca attattacct ccacggggag agcctgagca aactggcctc   1620
aggcatttga gaagcacacg gtcacactgc ttccggtagt caataaaccg gtaaaccagc   1680
aatagacata agcggctatt taacgaccct gccctgaacc gacgaccggg tcgaatttgc   1740
tttcgaattt ctgccattca tccgcttatt atcacttatt caggcgtagc accaggcgtt   1800
taagggcacc aataactgcc ttaaaaaaat tacgccccgc cctgccactc atcgcagtac   1860
tgttgtaatt cattaagcat tctgccgaca tggaagccat cacagacggc atgatgaacc   1920
tgaatcgcca gcggcatcag caccttgtcg ccttgcgtat aatatttgcc catggtgaaa   1980
acgggggcga agaagttgtc catattggcc acgtttaaat caaaactggt gaaactcacc   2040
cagggattgg ctgagacgaa aaacatattc tcaataaacc ctttagggaa ataggccagg   2100
ttttcaccgt aacacgccac atcttgcgaa tatatgtgta gaaactgccg gaaatcgtcg   2160
tggtattcac tccagagcga tgaaaacgtt tcagtttgct catggaaaac ggtgtaacaa   2220
gggtgaacac tatcccatat caccagctca ccgtctttca ttgccatacg aaattccgga   2280
tgagcattca tcaggcgggc aagaatgtga ataaaggccg gataaaactt gtgcttattt   2340
ttctttacgg tctttaaaaa ggccgtaata tccagctgaa cggtctggtt ataggtacat   2400
tgagcaactg actgaaatgc ctcaaaatgt tctttacgat gccattggga tatatcaacg   2460
gtggtatatc cagtgatttt tttctccatt ttagcttcct tagctcctga aaatctcgat   2520
aactcaaaaa atacgcccgg tagtgatctt atttcattat ggtgaaagtt ggaacctctt   2580
acgtgccgat caacgtctca ttttcgccaa aagttggccc agggcttccc ggtatcaaca   2640
gggacaccag gatttattta ttctgcgaag tgatcttccg tcacaggtat ttattcggcg   2700
caaagtgcgt cgggtgatgc tgccaactta ctgatttagt gtatgatggt gtttttgagg   2760
tgctccagtg gcttctgttt ctatcagctg tccctcctgt tcagctactg acggggtggt   2820
gcgtaacggc aaaagcaccg ccggacatca gcgcctgtag tgccatttac cccccattcac  2880
```

-continued

```
tgccagagcc gtgagcgcag cgaactgaat gtcacgaaaa agacagcgac tcaggtgcct   2940
gatggtcgga gacaaaagga atattcagcg atttgcccga gcttgcgagg gtgctactta   3000
agcctttagg gttttaaggt ctgttttgta gaggagcaaa cagcgtttgc gacatccttt   3060
tgtaatactg cggaactgac taaagtagtg agttatacac agggctggga tctattcttt   3120
ttatcttttt ttattctttc tttattctat aaattataac cacttgaata taaacaaaaa   3180
aaacacacaa aggtctagcg gaatttacag agggtctagc agaatttaca agttttccag   3240
caaaggtcta gcagaattta cagataccca caactcaaag gaaaaggact agtaattatc   3300
attgactagc ccatctcaat tggtatagtg attaaaatca cctagaccaa ttgagatgta   3360
tgtctgaatt agttgttttc aaagcaaatg aactagcgat tagtcgctat gacttaacgg   3420
agcatgaaac caagctaatt ttatgctgtg tggcactact caaccccacg attgaaaacc   3480
ctacaaggaa agaacggacg gtatcgttca cttataacca atacgctcag atgatgaaca   3540
tcagtaggga aaatgcttat ggtgtattag ctaaagcaac cagagagctg atgacgagaa   3600
ctgtggaaat caggaatcct ttggttaaag gctttgagat tttccagtgg acaaactatg   3660
ccaagttctc aagcgaaaaa ttagaattag tttttagtga agagatattg ccttatcttt   3720
tccagttaaa aaaattcata aaatataatc tggaacatgt taagtctttt gaaaacaaat   3780
actctatgag gatttatgag tggttattaa aagaactaac acaaaagaaa actcacaagg   3840
caaatataga gattagcctt gatgaattta agttcatgtt aatgcttgaa aataactacc   3900
atgagtttaa aaggcttaac caatgggttt tgaaaccaat aagtaaagat ttaaacactt   3960
acagcaatat gaaattggtg gttgataagc gaggccgccc gactgatacg ttgattttcc   4020
aagttgaact agatagacaa atggatctcg taaccgaact tgagaacaac cagataaaaa   4080
tgaatggtga caaaatacca acaaccatta catcagattc ctacctacgt aacggactaa   4140
gaaaaacact acacgatgct ttaactgcaa aaattcagct caccagtttt gaggcaaaat   4200
ttttgagtga catgcaaagt aagcatgatc tcaatggttc gttctcatgg ctcacgcaaa   4260
aacaacgaac cacactagag aacatactgg ctaaatacgg aaggatctga ggttcttatg   4320
gctcttgtat ctatcagtga agcatcaaga ctaacaaaca aaagtagaac aactgttcac   4380
cgttagatat caaagggaaa actgtccata tgcacagatg aaaacggtgt aaaaaagata   4440
gatacatcag agcttttacg agtttttggt gcatttaaag ctgttcacca tgaacagatc   4500
gacaatgtaa cagatgaaca gcatgtaaca cctaatagaa caggtgaaac cagtaaaaca   4560
aagcaactag aacatgaaat tgaacacctg agacaacttg ttacagctca acagtcacac   4620
atagacagcc tgaaacaggc gatgctgctt atcgaatcaa agctgccgac aacacgggag   4680
ccagtgacgc ctcccgtggg gaaaaaatca tggcaattct ggaagaaata gcgcccaata   4740
cgcaaaccgc ctctccccgc gcgttggccg attcattaat gcagctggca cgacaggttt   4800
cccgactgga aagcgggcag tgagcgcaac gcaattaatg tgagttagct cactcattag   4860
gcaccccagg ctttacactt tatgcttccg gctcgtatgt tgtgtggaat tgtgagcgga   4920
taacaatttc acacaggaaa cagct                                         4945
```

<210> SEQ ID NO 7
<211> LENGTH: 1200
<212> TYPE: DNA
<213> ORGANISM: Pseudomonas
<220> FEATURE:
<223> OTHER INFORMATION: formaldehyde dismutase Ile-301-Leu -continued

<400> SEQUENCE: 7

```
atggcgggta ataaatcggt ggtgtatcat ggtacccgcg acctgcgtgt tgaaaccgtg      60
ccgtatccga agctggaaca taacaaccgt aaactggaac acgcagttat ccttaaagtt     120
gtgagcacca acatttgtgg tagcgatcag catatttacc gcggccgctt tattgtgccg     180
aaaggccatg ttttaggcca cgaaattacc ggcgaagtcg tggaaaaagg cagtgatgtt     240
gaactgatgg atattggcga tctggtatcc gtgccgttta acgtcgcgtg cggtcgttgc     300
cggaactgta aggaagcccg cagcgatgtg tgcgaaaaca atcttgtgaa ccccgatgcg     360
gatctgggtg cgtttggctt tgatctgaaa gggtggagcg gaggtcaagc ggagtacgtt     420
ctcgtgcctt atgcggatta catgctgctg aaatttggcg ataaagagca agccatggaa     480
aaaattaaag atctgaccct gatctcggat atcctgccaa cgggttttca tggctgcgtt     540
tctgccggtg ttaagcctgg cagccatgtc tatattgcgg gcgcaggtcc agtcggtcgc     600
tgtgcagccg cgggtgcgcg cctgctgggc gccgcatgcg tgatcgtggg ggaccagaac     660
ccggagcgtc tcaaactgtt gtctgatgcc ggctttgaaa ccattgactt acgcaatagt     720
gcgccgctgc gtgatcagat cgatcagatc ttaggcaaac cggaagtgga ctgcggcgtg     780
gatgcggtgg gcttcgaagc acatggctta ggtgatgaag ccaatactga gacgccgaac     840
ggcgccctga acagcttgtt cgacgtggtg cgcgctgggg gcgctattgg tattccgggt     900
ctgtatgtcg ggtctgatcc ggatccggtg aacaaagatg ccggctccgg ccgcctgcac     960
ttggatttcg gcaaaatgtg gaccaaatcc attcgtatca tgacggggat ggcgccagtt    1020
actaattata accgtcatct gacggaagcg attctgtggg accagatgcc gtatctgtcg    1080
aaagtaatga acatcgaagt tattaccctg gaccaggcgc cggatggtta tgcgaaattt    1140
gataaaggca gtccggcgaa atttgtgatt gatccacatg gcatgttgaa aaataaataa    1200
```

<210> SEQ ID NO 8
<211> LENGTH: 399
<212> TYPE: PRT
<213> ORGANISM: Pseudomonas
<220> FEATURE:
<223> OTHER INFORMATION: formaldehyde dismutase Ile-301-Leu

<400> SEQUENCE: 8

```
Met Ala Gly Asn Lys Ser Val Val Tyr His Gly Thr Arg Asp Leu Arg
1               5                   10                  15

Val Glu Thr Val Pro Tyr Pro Lys Leu Glu His Asn Asn Arg Lys Leu
            20                  25                  30

Glu His Ala Val Ile Leu Lys Val Val Ser Thr Asn Ile Cys Gly Ser
        35                  40                  45

Asp Gln His Ile Tyr Arg Gly Arg Phe Ile Val Pro Lys Gly His Val
    50                  55                  60

Leu Gly His Glu Ile Thr Gly Glu Val Val Glu Lys Gly Ser Asp Val
65                  70                  75                  80

Glu Leu Met Asp Ile Gly Asp Leu Val Ser Val Pro Phe Asn Val Ala
                85                  90                  95

Cys Gly Arg Cys Arg Asn Cys Lys Glu Ala Arg Ser Asp Val Cys Glu
            100                 105                 110

Asn Asn Leu Val Asn Pro Asp Ala Asp Leu Gly Ala Phe Gly Phe Asp
        115                 120                 125

Leu Lys Gly Trp Ser Gly Gly Gln Ala Glu Tyr Val Leu Val Pro Tyr
    130                 135                 140
```

-continued

```
Ala Asp Tyr Met Leu Leu Lys Phe Gly Asp Lys Glu Gln Ala Met Glu
145                 150                 155                 160

Lys Ile Lys Asp Leu Thr Leu Ile Ser Asp Ile Leu Pro Thr Gly Phe
                165                 170                 175

His Gly Cys Val Ser Ala Gly Val Lys Pro Gly Ser His Val Tyr Ile
            180                 185                 190

Ala Gly Ala Gly Pro Val Gly Arg Cys Ala Ala Ala Gly Ala Arg Leu
        195                 200                 205

Leu Gly Ala Ala Cys Val Ile Val Gly Asp Gln Asn Pro Glu Arg Leu
    210                 215                 220

Lys Leu Leu Ser Asp Ala Gly Phe Glu Thr Ile Asp Leu Arg Asn Ser
225                 230                 235                 240

Ala Pro Leu Arg Asp Gln Ile Asp Gln Ile Leu Gly Lys Pro Glu Val
                245                 250                 255

Asp Cys Gly Val Asp Ala Val Gly Phe Glu Ala His Gly Leu Gly Asp
            260                 265                 270

Glu Ala Asn Thr Glu Thr Pro Asn Gly Ala Leu Asn Ser Leu Phe Asp
        275                 280                 285

Val Val Arg Ala Gly Gly Ala Ile Gly Ile Pro Gly Leu Tyr Val Gly
    290                 295                 300

Ser Asp Pro Asp Pro Val Asn Lys Asp Ala Gly Ser Gly Arg Leu His
305                 310                 315                 320

Leu Asp Phe Gly Lys Met Trp Thr Lys Ser Ile Arg Ile Met Thr Gly
                325                 330                 335

Met Ala Pro Val Thr Asn Tyr Asn Arg His Leu Thr Glu Ala Ile Leu
            340                 345                 350

Trp Asp Gln Met Pro Tyr Leu Ser Lys Val Met Asn Ile Glu Val Ile
        355                 360                 365

Thr Leu Asp Gln Ala Pro Asp Gly Tyr Ala Lys Phe Asp Lys Gly Ser
    370                 375                 380

Pro Ala Lys Phe Val Ile Asp Pro His Gly Met Leu Lys Asn Lys
385                 390                 395
```

<210> SEQ ID NO 9
<211> LENGTH: 1200
<212> TYPE: DNA
<213> ORGANISM: Pseudomonas
<220> FEATURE:
<223> OTHER INFORMATION: formaldehyde dismutase Phe-93-Ala / Ile-301-Leu

<400> SEQUENCE: 9

```
atggcgggta ataaatcggt ggtgtatcat ggtacccgcg acctgcgtgt tgaaaccgtg     60

ccgtatccga agctggaaca taacaaccgt aaactggaac acgcagttat ccttaaagtt    120

gtgagcacca acatttgtgg tagcgatcag catatttacc gcggccgctt tattgtgccg    180

aaaggccatg ttttaggcca cgaaattacc ggcgaagtcg tggaaaaagg cagtgatgtt    240

gaactgatgg atattggcga tctggtatcc gtgccggcga acgtcgcgtg cggtcgttgc    300

cggaactgta aggaagcccg cagcgatgtg tgcgaaaaca atcttgtgaa ccccgatgcg    360

gatctgggtg cgtttggctt tgatctgaaa gggtggagcg gaggtcaagc ggagtacgtt    420

ctcgtgcctt atgcggatta catgctgctg aaatttggcg ataaagagca agccatggaa    480

aaaattaaag atctgaccct gatctcggat atcctgccaa cgggttttca tggctgcgtt    540

tctgccggtg ttaagcctgg cagccatgtc tatattgcgg gcgcaggtcc agtcggtcgc    600

tgtgcagccg cgggtgcgcg cctgctgggc gccgcatgcg tgatcgtggg ggaccagaac    660
```

-continued

```
ccggagcgtc tcaaactgtt gtctgatgcc ggctttgaaa ccattgactt acgcaatagt    720

gcgccgctgc gtgatcagat cgatcagatc ttaggcaaac cggaagtgga ctgcggcgtg    780

gatgcggtgg gcttcgaagc acatggctta ggtgatgaag ccaatactga gacgccgaac    840

ggcgccctga acagcttgtt cgacgtggtg cgcgctgggg gcgctattgg tattccgggt    900

ctgtatgtcg ggtctgatcc ggatccggtg aacaaagatg ccggctccgg ccgcctgcac    960

ttggatttcg gcaaaatgtg gaccaaatcc attcgtatca tgacggggat ggcgccagtt   1020

actaattata accgtcatct gacggaagcg attctgtggg accagatgcc gtatctgtcg   1080

aaagtaatga acatcgaagt tattaccctg gaccaggcgc cggatggtta tgcgaaattt   1140

gataaaggca gtccggcgaa atttgtgatt gatccacatg gcatgttgaa aaataaataa   1200
```

```
<210> SEQ ID NO 10
<211> LENGTH: 399
<212> TYPE: PRT
<213> ORGANISM: Pseudomonas
<220> FEATURE:
<223> OTHER INFORMATION: formaldehyde dismutase Phe-93-Ala / Ile-301-Leu

<400> SEQUENCE: 10

Met Ala Gly Asn Lys Ser Val Val Tyr His Gly Thr Arg Asp Leu Arg
1               5                   10                  15

Val Glu Thr Val Pro Tyr Pro Lys Leu Glu His Asn Asn Arg Lys Leu
            20                  25                  30

Glu His Ala Val Ile Leu Lys Val Val Ser Thr Asn Ile Cys Gly Ser
        35                  40                  45

Asp Gln His Ile Tyr Arg Gly Arg Phe Ile Val Pro Lys Gly His Val
    50                  55                  60

Leu Gly His Glu Ile Thr Gly Glu Val Val Glu Lys Gly Ser Asp Val
65                  70                  75                  80

Glu Leu Met Asp Ile Gly Asp Leu Val Ser Val Pro Ala Asn Val Ala
                85                  90                  95

Cys Gly Arg Cys Arg Asn Cys Lys Glu Ala Arg Ser Asp Val Cys Glu
            100                 105                 110

Asn Asn Leu Val Asn Pro Asp Ala Asp Leu Gly Ala Phe Gly Phe Asp
        115                 120                 125

Leu Lys Gly Trp Ser Gly Gly Gln Ala Glu Tyr Val Leu Val Pro Tyr
    130                 135                 140

Ala Asp Tyr Met Leu Leu Lys Phe Gly Asp Lys Glu Gln Ala Met Glu
145                 150                 155                 160

Lys Ile Lys Asp Leu Thr Leu Ile Ser Asp Ile Leu Pro Thr Gly Phe
                165                 170                 175

His Gly Cys Val Ser Ala Gly Val Lys Pro Gly Ser His Val Tyr Ile
            180                 185                 190

Ala Gly Ala Gly Pro Val Gly Arg Cys Ala Ala Ala Gly Ala Arg Leu
        195                 200                 205

Leu Gly Ala Ala Cys Val Ile Val Gly Asp Gln Asn Pro Glu Arg Leu
    210                 215                 220

Lys Leu Leu Ser Asp Ala Gly Phe Glu Thr Ile Asp Leu Arg Asn Ser
225                 230                 235                 240

Ala Pro Leu Arg Asp Gln Ile Asp Gln Ile Leu Gly Lys Pro Glu Val
                245                 250                 255

Asp Cys Gly Val Asp Ala Val Gly Phe Glu Ala His Gly Leu Gly Asp
            260                 265                 270
```

-continued

```
Glu Ala Asn Thr Glu Thr Pro Asn Gly Ala Leu Asn Ser Leu Phe Asp
        275                 280                 285

Val Val Arg Ala Gly Gly Ala Ile Gly Ile Pro Gly Leu Tyr Val Gly
    290                 295                 300

Ser Asp Pro Asp Pro Val Asn Lys Asp Ala Gly Ser Gly Arg Leu His
305                 310                 315                 320

Leu Asp Phe Gly Lys Met Trp Thr Lys Ser Ile Arg Ile Met Thr Gly
                325                 330                 335

Met Ala Pro Val Thr Asn Tyr Asn Arg His Leu Thr Glu Ala Ile Leu
            340                 345                 350

Trp Asp Gln Met Pro Tyr Leu Ser Lys Val Met Asn Ile Glu Val Ile
        355                 360                 365

Thr Leu Asp Gln Ala Pro Asp Gly Tyr Ala Lys Phe Asp Lys Gly Ser
    370                 375                 380

Pro Ala Lys Phe Val Ile Asp Pro His Gly Met Leu Lys Asn Lys
385                 390                 395
```